US009365904B2

(12) United States Patent
Daum et al.

(10) Patent No.: US 9,365,904 B2
(45) Date of Patent: Jun. 14, 2016

(54) ION TORRENT GENOMIC SEQUENCING

(71) Applicant: Longhorn Vaccines and Diagnostics, LLC, Bethesda, MD (US)

(72) Inventors: Luke T. Daum, San Antonio, TX (US); Gerald W. Fischer, Bethesda, MD (US)

(73) Assignee: Longhorn Vaccines and Diagnostics, LLC, Bethesda, MD (US)

( * ) Notice: Subject to any disclaimer, the term of this patent is extended or adjusted under 35 U.S.C. 154(b) by 95 days.

(21) Appl. No.: 13/890,512

(22) Filed: May 9, 2013

(65) Prior Publication Data

US 2013/0302789 A1  Nov. 14, 2013

Related U.S. Application Data

(60) Provisional application No. 61/737,250, filed on Dec. 14, 2012, provisional application No. 61/695,960, filed on Aug. 31, 2012, provisional application No. 61/646,060, filed on May 11, 2012, provisional application No. 61/644,876, filed on May 9, 2012.

(51) Int. Cl.
*C12P 19/34* (2006.01)
*C12Q 1/70* (2006.01)
*C12Q 1/68* (2006.01)

(52) U.S. Cl.
CPC ............... *C12Q 1/701* (2013.01); *C12Q 1/689* (2013.01); *C12Q 1/6869* (2013.01); *C12Q 2600/156* (2013.01)

(58) Field of Classification Search
CPC ........... C12Q 1/6869; C12Q 2563/113; C12Q 2563/116; C12Q 1/689; C12Q 1/701; C12Q 2600/156
USPC .......................................................... 435/6.1
See application file for complete search history.

(56) References Cited

U.S. PATENT DOCUMENTS

| | | | |
|---|---|---|---|
| 5,550,040 A | 8/1996 | Purohit et al. | |
| 6,124,098 A | 9/2000 | Heym et al. | |
| 2009/0233292 A1 | 9/2009 | Podini et al. | |
| 2011/0207135 A1* | 8/2011 | Faham ................. | C12Q 1/6883 435/6.11 |
| 2011/0281754 A1 | 11/2011 | Fischer et al. | |
| 2011/0281776 A1* | 11/2011 | Eshoo ................... | B01L 3/5027 506/40 |
| 2012/0034685 A1 | 2/2012 | Sparks et al. | |
| 2012/0037531 A1 | 2/2012 | Pollner et al. | |
| 2012/0295819 A1* | 11/2012 | Leamon et al. ................. | 506/26 |

FOREIGN PATENT DOCUMENTS

| | | |
|---|---|---|
| CN | 102250924 | 11/2011 |
| WO | WO03/080870 | 10/2003 |
| WO | WO2006/110855 | 10/2006 |
| WO | WO2012/037531 | 3/2012 |

OTHER PUBLICATIONS

Ross et al., Am. J. Clin. Pathol. vol. 136, pp. 527-539, Oct. 2011.*
PCT Search and Patentability Report for PCT/US2013/040302, dated Oct. 4, 2013.
Howden, et al., "Evolution of Multidrug Resistance during *Staphylococcus aureus* Infection Involves Mutation of the Essential Two Component Regulator WalKR," PLoS Pathogens, vol. 7, No. 11, e1002359, pp. 1-15, Nov. 10, 2011.
Daum, et al., "Next-Generation Ion Torrent Sequencing of Drug Resistance Mutations in *Mycobacterium tuberculosis* Strains," Journal of Clinical Microbiology, vol. 50, No. 12, pp. 3831-3837, Sep. 12, 2012.
Daum, et al., "Genetic analysis of *Mycobacterium tuberculosis* drug-resistance genes from samples shipped in PrimerStore MTM and sequenced using the next-generation Ion Torrent," p. 1, www.lhnvd. com, retrieved on Jul. 1, 2015.
Mellmann, et al, "Prospective genomic characterization of the German enterohemorrhagic *Escherichia coli* 0104:H4 outbreak by rapid next generation sequencing technology," PLOS ONE, vol. 6, No. 7, Jul. 20, 2011.
Jun-Ichiro Sekiguchi, et al, "Detection of 1-3, 6, 10 multidrug resistance in *Mycobacterium tuberculosis*," Journal of Clinical Microbiology, American Society for Microbiology, vol. 45, No. 1, Jan. 1, 2007.
EP Search Report for PCTUS2013/040302, dated Oct. 8, 2015.
Daum, et al., "Characterization of multi-drug resistant *Mycobacterium tuberculosis* from immigrants residing in the USA using Ion Torrent full-gene sequencing," Epidemiology and Infection, vol. 142, No. 06, ogs. 1328-1333, Sep. 27, 2013.
Grabensteiner, et al, "Development of a multiplex RT-PCR for the simultaneous detection of three viruses of the honeybee (*Apis mellifera* L.): Acute bee paralysis virus, Black queen cell virus and Sacbrood virus," Journal of Invertebrate Pathology, vol. 94, No. 3, Feb. 14, 2007.
Canada Office Action for PCTUS2013/040302, dated Oct. 5, 2015.
Chinese Office Action for PCT/US2013/040302, dated Aug. 25, 2015.

* cited by examiner

Primary Examiner — Cynthia B Wilder
(74) Attorney, Agent, or Firm — Remenick PLLC

(57) ABSTRACT

Disclosed is an enhanced method for rapid and cost-effective analysis of sequences of a microorganism by semi-conductor sequencing, preferably ion-torrent sequencing. This method provides for full length analysis and of multiple areas (e.g. genes) of multiple genomes. These methods identify genetic mutations of a particular gene that are responsible for conferring resistance or sensitivity to an antibiotic or other chemical compound. Multiple different species, strains and/or serotypes of a particular organism are rapidly and efficiently screened and mutations identified along with the complete genome of an organism. By selecting primers pairs of similar size and GC content that produce amplicons with sequences spanning the entire genome, a single PCR reaction analyzed by ion torrent methodology can determine the sequence of a complete genome. Methods are useful to sequences the genomes of viral agents, such as influenza virus, and bacterial agents, such as tuberculosis bacteria.

19 Claims, 17 Drawing Sheets pncA gene + 100 flanking base pairs (1161 nt)

AGGCGGGAATGACACCGTCATCGCAGTCGAGTTCGAGATCGACAGCCGTGCCCGGAGCACCACCGCAGCCGCCCGATGAACGTGATATCCGAGATTCCGAGTCCAGATCCGATGAACGTGGAACGTGATAATCCAGATCGAAGGCGTCGTAGAAGCGG
CCGATGCCTCATGCCCGGTCCTGAGCTCCAAACCACTGAACCAACAACCGGAACCCGACCCGGTCTTGCAGGCTTCGAAAACCCGGTTCTTCGCCGGAGGCGTTCCACCCGGCCAACAGTTC
ATCCCGGTTCGGCGGTCGCATCAGAGCTCAAACCAATGAACCGACTCCTCCAGCCGACGGCTGTACCAGCCGGTCCGACGCTGTATCAGGTCGTTCAGCGTGCATGGCCAATCAGCGCTGAAGCCGCTGCGGCAAGCCGCTGTACGCTC
TACGCCGGTCCTCGGCCGTCGGGCCGCCGTTTGTAGAACACCGGCTTGTTCCGGACGCCGAATGTCCGCTGAATTCCGACAGTGACGTGCGGTGCCGCGAGTACCAGCAGCGATGCCGGTCTCTTCGAACGCTGTACGCTC
CGGTGTAGGCACGCCTTGTTGCACCCGGCCGGTCCCAATTGAACGCTGTCCGACATGGATCGGAAAGTCCCGATTCGGAGAAGTCCGATATGGCATGGAACAATAGTCCGGTGTGCAGGAATAGTCGTGGGAATAGCGGCATTTCGCCGAGAAGTCGGTCACC
GGGTGATGCGGAAGTCCTTGGTTCGCACAGTGCCCATCACGTCGAATCAGATCCGCTCTTGCACCACTAGGTGAGGCGCGTGGACCACCGCATCCCAGGTTACCGCGCCAGCCGTTCGAACATGAGCCGCCTAGCAGCCGCTTGACGGCCATGCCGATC
GACGATCATCAACCGCCGATAGGCCATACGCTCCAACAGCCCGTGATGTAGTGAGCGACAATCGTCGCAGCAGCCTTCGGCTCGACGCGATAATAGGCCCCCTATAGCCCACGCAGTCGAGCCCGAACATGACCAGCTCAGCGGCCACC
CAACCCGGATAGAATCACGCCGGAACATGCAGCCACATCGCGGTC (SEQ ID NO: 14)
CCCCATATCACCCGCCGGAACATCAGCCACATCGCGGTC

REVERSE COMPLEMENT

GACGCGACGATGTGGCTGACTGTCGCGGTGATTATTCGGTCGGTTGATATCGGCGGATCGGCGCTAGGCGGGTTGGACTGCGGTGACTGCGCCGTGACGAGGCGTTGGAGGCGTTGGACTGGCGGGATGACACCTTCTGTCACC**GACGGATTT
GTCGCTCACTAC**CTCAGTTGTGACACTATGCGGACTGACATCACGTCGTCTCAGTCTCCGCGGATCGTCCGACGGTGGTCATGTTCCGGATGTCTCGCGGATCGCGGGTCATCTTCCGGATCCGTGGACTGTAGGCAAACTGCCCGGACAGTCG
CCCGAAGCTATAGGCGACTATTGCGACGGTCCCAGACAACGACTTCTCCGAGAACGACTACCATCCCGCCGACACCGGTCTGCTCTCGTGGACCACTATTCCGGCGGACTTGCATCCAGTCGAGTCAATGGCGTCCTCGCCGGAAGCCGGCGCTGGACAC
TACCATCACGTCGTCTGGCAACCGAGCCGGTCTTCTCCAAGGCGTCCGTCTACAAGGCTTACAAGAGGTGCCACCCGGTCTGACGAGCCGGTTGGCAAGCGGCGACCGCACCAGCATGTAGACTGGATCGGGATTCATCCCTGCCAGTTCTCATCCCAGTCTTGGACAAGACTGGTCTGGTATTG
GTCATCACGTCGGACGAGCAGTCGAGGCGGTTCTTGCCACTCCTGAGCCAGAACCAGGACGCACCGGTACGAGGTACGGATCCGATATACCGGCCGTCGTGTGCCGATACCACCGCCTGCGTCGGCTGCGCTGGTTGTGCACCGCAGGCACTGCCCAGCGTC
CAGTTGGTTTGCAGCTGTCCTCGTCCCAGCACCCGACGCAGTCGGGCATGGCGGGGAGGCGGTGGAACCCGCGATCGAGGCGGCCGGAACTCCGTCATCCCCGGGATCGAGGCGGCCCGATGCGGACTCCGCGCGGGATCCCCGCCATTCCGCCATCGACTCAGTCGAACTCGA
CGGCGGCCCATCGGATGTGTGTGAATGCTGCCCTGCCCATGAGTGAAGCCCTCGCCCCGGCGCCGCCATCGACTCAGTCGAACTCGA
GGTGCCATGACTCGGTGATTCATTCCGGCT (SEQ ID NO: 15)

PROTEIN SEQUENCE

MRALIIVDVQNDFCEGGSLAVTGGAALARAISDVLAEAADYHHVAIKDFHIDPGDHFSGTPDYSSSWPHCVSGTPGADEHPSLDPSAIEAVEYKGAVTGAYSGFEGVDENGTPLLNWLRQRGVDEVDVGLAIDHCVR
QIAEDAVRNGLAIPRVMLDLTAGVSADTTVAALEMRTASVELVCSS (SEQ ID NO: 16)
Primer Length:

Forward 1 (20 nt): TCATGGACCCTATATCTGTG  (SEQ ID NO: 17)
Reverse 1 (20 nt): ATGAACTGTTGGCGGCGGTC  (SEQ ID NO: 18)
Amplicon Length: 675 nt Forward 2 (20 nt): ACGGATTTGTCGCTCACTAC  (SEQ ID NO: 19)
Reverse 2 (20 nt): ATCTGGATATCGTCCGGGC  (SEQ ID NO: 20)
Amplicon Length: 959 nt

FIG. 1

From H37Rv Gene strain

GCCCATCGTCGTTGATGCGGCGTTGTGGGGCGCCTGGCCCGTTTGTTTTGTCAGGATATTCGAATAACCTGGCCGCCCGTTTCCAAAGGGAGCGGTTGGGTTTGTTGGAGAGTTTGATCCTGGCTC
AGGACGAACGCTGGCGGCGTGCTTAACACATGCAAGTCGAACGGAAAGCTCTCTTCGGAGATACTCGAGTGGCGAACGGGTGAGTAACACGTGGGTAATCTGCCCTGCACTTCGGGATAAGCCTGGGA
AACTGGGTCTAATACCGGATAGGACCACGGGATGCATGTCTTGTGGTGGAAAGCGCTTTAGCGGTGTGGGATGAGCCCGCGGCCTATCAGCTTGTTGGTGGGGTGATGGCCTACCAAGCGACGACGC
GTAGCCGGCCTGAGAGGGTGTCCGGCCACACTGGGACTGAGATACGGCCCAGACTCCTACGGGAGGCAGCAGTGGGGAATATTGCACAATGGGCGCAAGCCTGATGCAGCGACGCCGCGTGGGGGATG
ACGGCCTTCGGGTTGTAAACCTCTTTCACCATCGACGAAGGTCCGGGTTCTCTCGGATTGACGGTAGGTGGAGAAGAAGCACCGGCCAACTACGTGCCAGCAGCCGCGGTAATACGTAGGGTGCGAGC
GTTGTCCGGAATTACTGGGCGTAAAGAGCTCGTAGGTGGTTTGTCGCGTTGTTCGTGAAATCTCACAGCTTAACTGTGGGCGTGCGGGCGATACGGGCAGACTAGAGTACTGCAGGGGAGACTGGAAT
TCCTGGTGTAGCGGTGGAATGCGCAGATATCAGGAGGAACACCGGTGGCGAAGGCGGGTCTCTGGGCAGTAACTGACGCTGAGGAGCGAAAGCGTGGGGAGCGAACAGGATTAGATACCCTGGTAGTC
CACGCCGTAAACGTTGGGCACTAGGTGTGGGGGACCTTCCACGGTTTCCGCGCCGTAGCTAACGCATAAGTGCCCCGCCTGGGGAGTACGGCCGCAAGGCTAAAACTCAAAGGAATTGACGGGGGCCC
GCACAAGCGGCGGAGCATGTGGATTAATTCGATGCAACGCGAAGAACCTTACCTGGGTTTGACATGCACAGGACGCGTCTAGAGATAGGCGTTCCCTTGTGGCCTGTGTGCAGGTGGTGCATGGCTG
TCGTCAGCTCGTGTCGTGAGATGTTGGGTTAAGTCCCGCAACGAGCGCAACCCTTGTCCTATGTTGCCAGCACGTAATGGTGGGGACTCGTAGGAGACTGCCGGGGTCAACTCGGAGGAAGGTGGGGA
CAACTCGCACCCGTGAAGTGGAGCTTCACACATGCTACAATGGCCGGTACAAAGGGCTGCGATGCCGCGAGGTTAAGCGAATCCTTAAAAGCCGGTCTCAGTTCGGATCGGGGTCTGCAACTCGACCCC
CAACTCGACCCGTGAAGTCGGAGTCGCTAGTAATCGCAGATCAGCAACGCTGCGGTGAATACGTTCCCGGGCCTTGTACACACCGCCCGTCACGTCATGAAAGTCGGTAACACCCGAAGCCAGTGGC
CTAACCCTCGGGAGGGAGCTGTCGAAGGTGGGATCGGCGATTGGGACGAAGTCGTAACAAGGTAGCCGTACCGGAAGGTGCGGCTGGATCACCTCCTTTCTAAGGAGCACCAGGAAACGCGGAAACT
GCTGGGCCGTAGGCCGTCGACGGGTTCTTGTCTGTACTGGCCGACGAGCCGGGATGCCAGGAAGTTGGGCA (SEQ ID NO: 2-)

TB 16S ribosomal RNA gene sequencing primers

PAIR 1:

For 16s Ver1: 5'-TGGCCGTTTTGTTTTGTCAGGAT-3' (SEQ ID NO: 22)

Rev16s Ver1: 5'-TACAGACAAGAACCCCTCACGG-3' (SEQ ID NO: 23)

Expected amplicon size: 1699 bp

PAIR 2:

For 16s Ver2: 5'-TTCTAAATACCTTTGGCTCCC-3' (SEQ ID NO: 1)

Rev 6s Ver2: 5'-TGGCCAACTTGTTGTCATCCA-3' (SEQ ID NO: 12)

Expected amplicon size: 1680 bp

FIG. 2 rpoB gene
Conferring sensitivities/resistance to Rifampin

GATCCGGACAGATCGTTCGCCGGCCGGCCCGAAAACCGACAAAATTATCGGGGCGAACCGGCCCCTGGGCACCGCTCCTCCTCGTTGCTCGCCATGAA
CCGCCAGAGCAAACAGCCCGTAGTCGACGTCGATCGGCTGGCTGATGGGTTCCTCGTCTCCAAACGTCGCCTTCCGCTGCTCAGGATAACCACTTGAGGTTCCGG
ACTCCTTGCACGTCCAGACCGATTCGTTCGAGTTGTCTTGATCGGTACCTTCGCCCGCTTCGGAGTGTTCAACCACTGGGTTGCTCTTAGAGCTGTC
CCGAGTTCACAACGAGAGACCATTCACACGGGTGTACTTCGAGAAGACAATTGATCGAGCCAGCACGTTCATCATCAACGGACCACAGCCAGCT
GTTGGCGGTGCCGGTGCCATGCGATGACGGATGGCGCAACGCAGATCGACCACCAGATCAACCTCGGCGCAATCTACCGCAGAGCCGCCCAT C TCGGT C TCCCAGA TCATGCGA TCGACGTGGACA
AGGACAACAACCGTCGCCGCCGGCGGTGAAACGACCGTCGAGGGCCGGT GACACCGAGAGCGTGTACGGCGGTCCGGTGTTGAAAGTGTTGCGTTTCGGCGAGCCGTGGTTGACACCGAGCATTGATC GCGAT CCGC GTGTACGGCCGGTCAGTCGT ACGC CGGTGCCGGTGTTGA
AGGTCATGTCCGGCGATGTCCGATGATGGCGACTGGCGC TGAGGGCCCCTCA AACGGT GCCATTGCCAAATCGTCGGCGATGGAGTTCTTCGGCAC
CAGCCAGTTGAG TCA[CAA]CCGGATGGTGATCGGGCCGATCGCCCAACATCGGCCAGCTCAAACGCAAGACGTTCGTCGGATCAGC
AGTGGTCGACGGCCTGGTTAGCGACGAGGAGGAGAACCGACCGGCCACCGTGGTGGTACACAGGCCAATTCGCCGATCGATGCGCCTTCGTCGGACGCCGCGCGC (SEQ ID NO: 24)

TB.rpoB. Forward Primer1: ACCGACAAAATTATCGGGCGA (SEQ ID NO: 25)

TB.rpoB. Reverse Primer1: ATCGATCGGCGAATTGGCCTGT (SEQ ID NO: 26)

Amplicon_length: 1718 bp

TB.rpoB. Forward Primer2: TCCTCTAAGGGCTCTCGTT (SEQ ID NO: 1)

TB.rpoB. Reverse Primer2: GTCAGGTACACGATCTCGT (SEQ ID NO: 2)

Amplicon_length: 1704 bp

FIG. 3

(SEQ ID NO: 27) TCGCGGGATCAAGCAGT = Reverse Primer from Article EID (Emerging Infectious Diseases) - 2001

(SEQ ID NO: 28) TGGAGGTCCGCGACGTGCA = Forward Primer from Article EID - 2001

TCG = codon 531 Serine to Luecine mutation

CAC = codon 526 Hisidine to Asparagine mutation

TCG = codon 522 Serine to Leucine mutation

GAC = codon 516 Aspartic acid to Valine

CAA = codon 513 Glutamine to Lysine

CTG = codon 533 Leucine to Proline

ATC = codon 572 Isoleucine to Phenylalanine

New Forward Primer

TB.rpoB. Forward Primer3: AATATCTGGTCCGCTTGCACGA (SEQ ID NO: 29)

With TB.rpoB.Reverse Primer is 620 bps

*FIG. 3*
*Continue*

Mycobacterium tuberculosis H37Ra, complete genome

GenBank: CP000611.1

GyrA Gene

GACGTCGACGCGCGGCGCAGCTTTATCACCCGCAACGCCAAGGATGTTCGGTTCCTGGATGTCTAACGCAACCCTGCGTTCGATTGCAAACGAGGAATAGATGACAGACACGACGTTGCCGCCTGACG
ACTCGCTCGACCGGATCGAACCGGTTCACATCGAGCAGGAGATGCAGCGCAGCTACATCGACTATGCGATGAGCGTGATCGTCGGCCGCGCGCTGCCGGAGGTGCGCGACGGCTCAAGCCCGTGCAT
CGCCGGGTGCTCTATGCAATGTTCGATTCCGGCTTCCGCCCGGACCGCAGCCACGCCAAGTCGGCCCGGTCGGTTGCCGAGACCATGGGCAACTACCACCCGCACGGCGACGCGTCGATCTACGACAG
CCTGGTGCGCATGGCCCAGCCCTGGTCGCTGCGCTACCCGCTGGTGGACGGCCAGGGCAACTTCGGCTCGCCAGGCAATGACCCACCGGCGGCGATGAGGTACACCGAAGCCCGGCTGACCCCGTTGG
CGATGGAGATGCTGAGGGAAATCGACGAGCAGACAGTCGATTTCATCCCTAACTACGACGGCCCGGTGCAAGAGCCGACGGTGCTACCCAGCCGGTTCCCCAACCTGCTGGCCAACGGTCAGGCGGC
ATCGCGGTCGGCATGGCAACCAATATCCCGCCGCACAACCTGCGTGAGCTGGCCGACGCGGTGTTCTGGGCGCTGGAGAATCACGACGCCGACGAAGAGGAGACCCTGGCCGCGGTCATGGGGCGGT
TAAAGGCCCGGACTTCCCGACCGCCGGACTGATCGTCGGATCCCAGGGCACCGCTGATGCCTACAAAACTGGCCGCGGCTCCATTCGAATGCGCGGAGTTGTTGAGGTAGAAGAGGATTCCCGCGGTC
GTACCTCGCTGGTGATCACCGAGTTGCCGTATCAGGTCAACCACGACAACTTCATCACTTCGATCGCCGAACAGGTCCGAGACGGCAAGCTGGCCGGCATTTCCAACATTGAGGACCAGTCTAGCGAT
CGGTCGGTTTACGCATCGTCATCGAGATCAAGCGCGATGCGGTGGCCAAGGTGGTGATCAATAACCTTTACAAGCACACCCAGCTGCAGACCAGCTTTGGCGCCAACATGCTAGCGATCGTCGACGG
GGTGCCGCGCACGCTGCGGCTGGACCAGCTGATCCGCTATTACGTTGACCACCAACTCGACGTCATTGTGCGGCGCACCACCTACCGGCTGCGCAAGGCAAACGAGCGAGCCCACATTCTGCGCGGCC
TGGTTAAAGCGCTCGACGCGCTGGACGAGGTCATTGCACTGATCCGGGCGTCGGAGACCGTCGATATCGCCCGGGCCGGACTGATCGAGCTGCTCGACATCGACGAGATCCAGGCCCAGGCAATCCTG
GACATGCAGTTGCGGCGCCTGGCCGCACTGGAACGCCAGCGCATCATCGACGACCTGGCCAAAATCGAGGCCGAGATCGCCGATCTGGAAGACATCCTGGCAAAACCCGAGCGGCAGCGTGGGATCGT
GCGCGACGAACTCGCCGAAATCGTGGACAGGCACGGCGACGACCGGCGTACCCGGATCATCGCGGCCGACGGAGACGTCAGCGACGAGGATTTGATCGCCCGCGAGGACGTCGTTGTCACTATCACCG
AAACGGGATACGCCAAGCGCACCAAGACCGATCTGTATCGCAGCCAGAAACGCGGCGGCAAGGGCGTGCAGGGTGCGGGCTTGAAGCAGGACGACATCGTCGCGCACTTCTTCGTGTGCTCCACCCAC
GATTTGATCCTGTTCTTCACCACCCAGGGACGGGTTTATCGGGCCAAGGCCTACGACTTGCCCGAGGCCTCCCGGACGGCGCCGCGGCAGCACGTGGCCAACCTGTTAGCCTTCCAGCCCGAGGAACG
CATCGCCCAGGTCATCCAGATTCGCGGCTACACCGACGCCCCGTACCTGGTGCTGGCCACTCGCAACGGGCTGGTGAAAAAGTCCAAGCTGACCGACTTCGACTCCAATCGCTCGGGCGGAATCGTGG
CGGTCAACCTGCGCGACAACGACGAGCTGGTCGGTGCGGTGCTGTGTTCGGCCGGCGACGACCTGCTGCTGGTCTCGGCCAACGGGCAGTCCATCAGGTTCTCGGCGACCGACGAGGCGCTGCGGCCA
ATGGGTCGTGCCACCTCGGGTGTGCAGGGCATGCGGTTCAATATCGACGACCGGCTGCTGTCGCTGAACGTCGTGCGTGAAGGCACCTATCTGCTGGTGGCGACGTCAGGGGGCTATGCGAAACGTAC
CGCGATCGAGGAATACCCGGTACAGGGCCGCGGCGGTAAAGGTGTGCTGACGGTCATGTACGACCGCCGGCGCGGCAGGTTGGTTGGGGCGTTGATTGTCGACGACGACAGCGAGCTGTATGCCGTCA
CTTCCGGCGGTGGCGTGATCCGCACCGCGGCACGCCAGGTTCGCAAGGCGGGACGGCAGACCAAGGGTGTTCGGTTGATGAATCTGGGCGAGGGCGACACACTGTTGGCCATCGCGCGCAACGCCGAA
GAAAGTGGCGACGATAATGCCGTGGACGCCAACGGCGCAGACCAGACGGGCAATTAATCAGGCTCGCCCGACGACGATGCGGATCGCGTAGCGATCTGAGGAGGAATCGGGCAGCTAGGCTCGGCAGC
CGGGTACGAGTGTTAGGAGTCGGGGTGAC (SEQ ID NO: 30)

FIG. 4

Primer Pair #1:

TB.GyrA.Forward1: CTAACGAACCTGCGTTGAT (22 bases) (SEQ ID NO: 31)
TB.GyrA.Reverse1: ATTCCTCTCAGATCGTACG (21 bases) (SEQ ID NO: 32)
Amplicon: 2605 bp Primer Pair #2:

TB.GyrA.Forward2: AAGGATGTTGGTTGCTGAT (21 bases) (SEQ ID NO: 9)
TB.GyrA.Reverse2: TAACATCG-ACCCGGCT (18 bases) (SEQ ID NO: 10)
Amplicon: 2703 bp FQ resistance is at codons 94 (Green) and perhaps 90.

TB.GyrA.Reverse3: CGTCCTAGT

Mycobacterium tuberculosis H37Ra, complete genome

GenBank: CP000611.1 catalase-peroxidase-peroxynitritase T katG

GTCTTGCCGGCGTTATCGCCGATGTCGACTGTGCTGTTGGCGAGGCACCCTGTCTGACGGCCTCGGACCATAACGGCTTCCTGTTGGACGAGCGGAGGTCATCTACTGGGGTCTATGTCCTGATTGTT
CGATATCCGACACTTCGCGATCACATCCGTGATCACAGCCCGATAACACCAACTCCTGGAAGGAATGCTGTGCCCGAGCAACACCCACCCATTACAGAAACCACCACCGGAGCCGCTAGCAACGGCTG
TCCCGTCGTGGTCATATGAAATACCCCGTCGAGGGCGGCGGAAACCAGGACTGGTGGCCCAACCGGCTCAATCTGAAGGTACTGCACCAAAACCCGGCCGTCGCTGACCCGATGGTGCGGCGTTCG
ACTATGCCGCGGAGGTCGCGACCATCGACGTTGACGCCCTGACGCGGGACATCGAGGAAGTGATGACCACCTCGCAGCCGTGGTGGCCCGCCGACTACGGCCACTACGGGCCGCTGTTTATCCGGATG
GCGTGGCACCGCTGCCGGCACCTACCGCATCCACGACGGCCGCGGCGGCGCCGGGGGCGGCATGCAGCGGTTCGCGCCGCTTAACAGCTGGCCCGACAACGCCAGCTTGGACAAGGCGCGCCGGCTGCT
GTGGCCGGTCAAGAAGAAGTACGGCAAGAAGCTCTCATGGGCGGACCTGATTGTTTTCGCCGGCAACTGCGCGCTGGAATCGATGGGCTTCAAGACGTTCGGGTTCGGCTTCGGCCGGGTCGACCAGT
GGGAGCCCGATGAGGTCTATTGGGGCAAGGAAGCCACCTGGCTCGGCGATGAGCGTTACAGCGGTAAGCGGGATCTGGAGAACCCGCTGGCCGCGGTGCAGATGGGGCTGATCTACGTGAACCCGGAG
GGGCCGAACGGCAACCCGGACCCCATGGCCGCGGCGGTCGACATTCGCGAGACGTTTCGGCGCATGGCCATGAACGACGTCGAAACAGCGGCGCTGATCGTCGGCGGTCACACTTTCGGTAAGACCCA
TGGCGCCGGCCCGGCCGATCTGGTCGGCCCCGAACCCGAGGCTGCTCCGCTGGAGCAGATGGGCTTGGGCTGGAAGAGCTCGTATGGCACCGGAACCGGTAAGGACGCGATCACCAGCGGCATCGAGG
TCGTATGCACGAACACCCCGACGAAATGGGACAACAGTTTCCTCGAGATCCTGTACGGCTACGAGTGGGAGCTGACGAAGAGCCCTGCTGGCGCTTGGCAATACACCGCCAAGGACGGCGCCGGTGCC
GGCACCATCCCGGACCCGTTCGGCGGGCCAGGCCGCTCCCCGACGATGCTGGCCACTGACCTCTCGCTGCGGGTGGATCCGATCTATGAGCGGATCACGCGTCGCTGGCTGGAACACCCCGAGGAATT
GGCCGACGAGTTCGCCAAGGCCTGGTACAAGCTCATCCACCGAGACATGGGTCCCGTTGCGAGATACCTTGGGCCGCTGGTCCCCAAGCAGACCCTGCTGTGGCAGGATCCGGTCCCTGCGGTCAGCC
ACGACCTCGTCGGCGAAGCCGAGATTGCCAGCCTTAAGAGCCAGATCCGGGCATCGGGATTGACTGTCTCACAGCTAGTTTCGACCGCATGGCGGCGGCGTCGTCGTTCCGTGGTAGCGACAAGCGC
GGCGGCGCCAACGGTGGTCGCATCCGCCTGCAGCCACAAGTCGGGTGGGAGGTCAACGACCCCGACGGGGATCTGCGCAAGGTCATTCGCACCCTGGAAGAGATCCAGGAGTCATTCAACTCCGCGGC
GCCGGGCAACATCAAAGTGTCCTTCGCCGACCTCGTCGTGCTCGGTGGCTGTGCCGCCATAGAGAAAGCAGCAAAGGCGGCTGGCCACAACATCACGGTGCCCTTCACCCCGGGCCGCACGGATGCGT
CGCAGGAACAAACCGACGTGGAATCCTTTGCCGTGCTGGAGCCCAAGGCAGATGGCTTCCGAAACTACCTCGGAAAGGGCAACCCGTTGCCGGCCGAGTACATGCTGCTCGACAAGGCGAACCTGCTT
ACGCTCAGTGCCCCTGAGATGACGGTGCTGGTAGGTGGCCTGCGCGTCCTCGGCGCAAACTACAAGCGCTTACCGCTGGGCGTGTTCACCGAGGCCTCCGAGTCACTGACCAACGACTTCTTCGTGAA
CCTGCTCGACATGGGTATCACCTGGGAGCCCTCGCCAGCAGATGACGGGACCTACCAGGGCAAGGATGGCAGTGGCAAGGTGAAGTGGACCGGCAGCCGCGTGGACCTGGTCTTCGGGTCCAACTCGG
AGTTGCGGGCGCTTGTCGAGGTCTATGGCGCCGATGACGCGCAGCCGAAGTTCGTGCAGGACTTCGTCGCTGCCTGGGACAAGGTGATGAACCTCGACAGGTTCGACGTGCGCTGATTCGGGTTGATC
GGCCCTGCCCGCCGATCAACCACAACCCGCCGCAGCACCCCGCGAGCTGACCGGCTCGCGGGTGCTGGTGTTTGCCCGGCGCGATTTGTCAGACCCCGCGTGCATGGTGGTCGCAGGCACGACGAGA
CGGGGATCACGAGACGGGGATGAGGAGAAAGGCCCCCGAAATGTGCTGGATGTGCGATCACCCGGAAGCCACCGCCGAGG (SEQ ID NO: 34)

TB.KatG-Forward1: TCGCGATCACATCCGTGATCAC (SEQ ID NO: 35)

TB.KatG-Reverse1: ATGCACGCGGGGTCTGACAAAT (SEQ ID NO: 36)

Amplicon Size: 2538 bp

*FIG. 5*

TB.KatG-Forward2: ACACCAACTCCTGGAAGGAAT (SEQ ID NO: 37) or ACACCAACTCCTGGGAAGGAAT (SEQ ID NO: 5)

TB.KatG-Reverse2: TCATCGCACATCCAGCACATT (SEQ ID NO: 6)

Amplicon Size: 2447 bp

The mutation is at Codon 315.

IN Wildtype it is Serine (S)

IN Beijing it is Gycine (G)

In others it is a Threonine (T)

New primers

TB.KatG-Forward3: TTACAGCCGTAAGCGGATCT (SEQ ID NO: 38)

TB.KatG-Reverse3: TTGCCGAACTCGTCGGCCAATT (SEQ ID NO: 39)

Amplicon size: 603 bp

FIG. 5
Continue

INFLUENZA A (H3N2) MASTER PRIMER LIST FOR ION TORRENT

| | SEQ ID NO: | LENGTH (bp): | MELTING TEMP C: | G/C % | AMPL. LENGTH (bp): | START POSITION: | END POSITION: |
|---|---|---|---|---|---|---|---|
| PB2 PRIMER SETS: | | | | | | | |
| FORWARD: ATT ATA TTC AGT ATG GAA AGA A | 40 | 22 | 44.5 | 22.7 | 943 | 1 | |
| REVERSE: ATA TAT CCA CAG CTT GTT C | 41 | 19 | 46.6 | 36.8 | | | 943 |
| FORWARD: GAT CCA CTA GCA TCT TTA TT | 42 | 20 | 46.9 | 35 | 997 | 835 | |
| REVERSE: GTA CGT CTC TCA TTT GTT | 43 | 18 | 46.5 | 38.9 | | | 1831 |
| FORWARD: AAG GCA TTT TCA GAA AGA T | 44 | 19 | 47 | 31.6 | 998 | 1336 | |
| REVERSE: GTC GTT TTT AAA CTA TTC AGC | 45 | 21 | 47.7 | 33.3 | | | 2314 |
| | | AVERAGE: | 46.5 | | 979 | | |
| PB1 PRIMER SETS: | | | | | | | |
| FORWARD: ACC ATT TGA ATG GAT GTC | 46 | 18 | 47.2 | 38.9 | 996 | 1 | |
| REVERSE: TTG ATT CTT TGT GAT GTA TGT | 47 | 21 | 47.5 | 28.6 | | | 996 |
| FORWARD: AAT GAT GAC TAA TTC ACA AG | 48 | 20 | 45.3 | 30 | 997 | 997 | |
| REVERSE: ATA ATT CTC ATC CAT CAG C | 49 | 19 | 46.7 | 36.8 | | | 1869 |
| FORWARD: AAA TAC ACC AAG ACA ACA TA | 50 | 20 | 46.6 | 30 | 1009 | 1316 | |
| REVERSE: CAT GAA GGA CAA GCT AAA T | 51 | 19 | 47.4 | 36.8 | | | 2311 |
| FORWARD: ATTTTGAATGGATGTCAATC | 52 | 20 | 46.2 | 30 | 913 | 3 | |
| REVERSE: GTGATTGTGAAAGAAAGCT | 53 | 19 | 48.1 | 36.8 | | | 916 |
| | | AVERAGE: | 46.8 | | 1001 | | |
| PA PRIMER SETS: | | | | | | | |
| FORWARD: CTG ATT CGA AAT GGA AGA | 54 | 18 | 46.6 | 38.9 | 989 | 1 | |
| REVERSE: CGT GTG GTT TGA CTA TAT | 55 | 18 | 46.3 | 38.9 | | | 989 |
| FORWARD: GAT CAA GTG CAT AAA AAC AT | 56 | 20 | | | 1001 | 931 | |
| REVERSE: ATA GAG TCC TAC AGA CTT T | 57 | 19 | 46.5 | 36.8 | | | 1931 |
| FORWARD: TGA CGA ACC TGA ATT AAG | 58 | 18 | 46.5 | 38.9 | 998 | 1212 | |
| REVERSE: GTA CGG ATA ACA AAT AGT AG | 59 | 20 | 44.9 | 35 | | | 2192 |
| | | AVERAGE: | 46.2 | | 996 | | |

*FIG. 10*

| | | | | | | |
|---|---|---|---|---|---|---|
| HA PRIMER SETS: | | | | | | |
| FORWARD: TAA TTC TAT TAA CCA TGA AGA C | 60 | 22 | 45.5 | 27.3 | 887 | 1 | 887 |
| REVERSE: GCA TCT GAT CTC ATT ATT G | 61 | 19 | 45.5 | 36.8 | | | |
| FORWARD: CAT ACT TTT GAT TAA CAG CA | 62 | 20 | 45.8 | 30 | 940 | 802 | 1722 |
| REVERSE: TTA ATG CAC TCA AAT GCA | 63 | 18 | 47.1 | 33.3 | | | |
| | | AVERAGE: | 46.0 | | 914 | | |
| NP PRIMER SETS: | | | | | | |
| FORWARD: AAT AAT CAC TCA CTG AGT G | 64 | 19 | 46.5 | 36.8 | 803 | 1 | 803 |
| REVERSE: AAT ATG AGA TCT TCG ATC TC | 65 | 20 | 46.1 | 35 | | | |
| FORWARD: ACA AGA AGT GCT TAT GAG | 66 | 18 | 46.5 | 38.9 | 859 | 690 | 1537 |
| REVERSE: TTC CTT AAT TGT CGT ACT C | 67 | 19 | 46.4 | 36.8 | | | |
| FORWARD: CTGAGTGACATCAAAATCA | 68 | 19 | 47.3 | 36.8 | 719 | 13 | |
| REVERSE: GCAGCTGTTTGAAATTTTC | 69 | 19 | 48.1 | 36.8 | | 731 | |
| | | AVERAGE: | 46.4 | | 831 | | |
| NA PRIMER SETS: | | | | | | |
| FORWARD: AAG ATG AAT CCA AAC CAA | 70 | 18 | 46.1 | 33.3 | 758 | 1 | 758 |
| REVERSE: GTA TCA GCT TTT CCT GAA | 71 | 18 | 46.5 | 38.9 | | | |
| FORWARD: GAT AGT GTT GTT TCA TGG | 72 | 18 | 45.3 | 38.9 | 790 | 657 | 1429 |
| REVERSE: CTA AAA TTG CGA AAG CTT ATA | 73 | 21 | 46.5 | 28.6 | | | |
| | | AVERAGE: | 46.1 | | 774 | | |
| M1/M2 PRIMER SETS: | | | | | | |
| FORWARD: ATA TTG AAA GAT GAG CCT T | 74 | 19 | 46 | 31.6 | 999 | 1 | 999 |
| REVERSE: TAG TTT TTT ACT CCA ACT CTA | 75 | 21 | 46 | 28.6 | | | |
| | | AVERAGE: | 46 | | 999 | | |
| NS1/NS2 PRIMER SETS: | | | | | | |
| FORWARD: ACA AAG ACA TAA TGG ATT CT | 76 | 20 | 46.5 | 30 | 863 | 1 | 863 |
| REVERSE: GGT GTT TTT TAT CAT CAA ATA AG | 77 | 23 | 46.4 | 26.1 | | | |
| | | AVERAGE: | 46.5 | | 863 | | |

FIG. 10
*Continue*

Coding region for pncA gene: SHADED

GACGGGATTGTGCGCTCACTACACATCACCGGGGTGATCTATCCCGCCGGTTGGGTTGCCGCCCCCTCAGCTGGCATGTTCGGCATCGTCTGCGGCCTGCCGCCGTCGGTA
GGCAAACTGCCCGGGACAGTCGCCGAACGTATGCGGACGTAGCGGCGTTGATCATCGTCGACGTGCAGAACGACATCGTCGAGGCGTACGCGGGTGGGCGGCACCGTGGCCGC
GCCATCAGCGACGACGGGCGACTATCAGTGCGGGGCGAGCCGGCAGACGATGTCGCCACATCCCAACACCAGCACCGGGTGCCTACGGAACCGGAGCTATTCGGCGCACCGGAGCGGGTGCTGCCGTGGCACCGGTGCACGCCGAGGACTATTG
CGTCAGCGCGTACTGCGGCCACGTCGAATGCGCCGGGCAAGGCTGCAATGAGTCGATCGAGTCAGGCTCCATCGGCCCCGGCAGCGACGACGAGCGGGCCACGCCCGAGGAGCGGGTCCTGGGTC
GACCTGAGCACGCCCGCAGCGTCGTGCCCGGCGATACCGCCCGCGATCTGCCGCGTGCCGGATGCCAGACATGCCCACCCCGCCCGCGCGTGCCCGGCACGCCCGACGCGTCGCCGGTC
GAGCGCTCGCCAAGCGGGCCGCCCGCCCCGGCCCGCTGCCGGCCTGTGGCTCACCGCAGCAGGGCCACCCCCGTGGGCTCCCACCCCGCAGGTGCACTGGCCCGGTTCGCCCGCTC
CTACGACACCCTTCATGGGCCGGCGATATCACGTTCCATCCGGATCTGGATCTGCTCCGGC (SEQ ID NO: 78)

FIG. 11A

GACGGATTTGTCGCTCAC = pncA.P1-Fwd (SEQ ID NO: 79)
AGCCACCCTCGCAGAA = pncA.P1-Rev (SEQ ID NO: 80)

CATCGTCGACGTGCAGAA = pncA.P2-Fwd (SEQ ID NO: 81)
TGTCCAGACTGGGATGGAA = pncA.P2-Rev (SEQ ID NO: 82)

ATTGCGTCAGGGGTAC = pncA.P3-Fwd (SEQ ID NO: 83)
TGGCCAAGCCATTGCGTA = pncA.P3-Rev (SEQ ID NO: 84)

ATCATTGTGTGCCCAGA = pncA.P4-Fwd (SEQ ID NO: 85)
CAACAGTTCATCCCGGTT = pncA.V2.P4-Rev (SEQ ID NO: 86)

PncA.P1: 221 bp

GACGGATTTGTCGCTCACTACATCACCGGCTGATCTA TCCGCGGGT GGGTGCCGCCCTCAGCTGC CATGTTCGGCA CGTCGCGGCC CATGGACCCTATATCTGTGGC TGCCGGCGTCGGTA (SEQ ID NO: 87)
GGCAAACATGCCCGGCAGTCGCCCGAACGTACGTATGGCAACGTATGGGAACGTATGGCGATGCGGGCGGTTGATCATCGTCGACGTGCAGAAGGACGTCGAGGAGGCAGGGTAGCGT

PncA.P2: 245 bp

SEQUENCE LISTING

<160> NUMBER OF SEQ ID NOS: 90

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 1
tcctctaagg gctctcgtt                                              19

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gtcaggtaca cgatctcgt                                              19

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
atcgaaacgc cgtaccgcaa                                             20

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
tgacgtcgag cacgtaactc cct                                         23

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
acaccaactc ctgggaagga at                                          22

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
tgatcgcaca tccagcacat tt                                          22

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
```

```
gacggatttg tcgctcacta c                                          21
```

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8

```
gccggagacg atatccagat                                            20
```

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9

```
aaggatgttc ggttcctgga t                                          21
```

<210> SEQ ID NO 10
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10

```
taacactcgt acccggct                                              18
```

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11

```
ttctaaatac ctttggctcc ct                                         22
```

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12

```
tggccaactt tgttgtcatg ca                                         22
```

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13

```
acgcgtgatc agcaaaagca gg                                              22
```

<210> SEQ ID NO 14
<211> LENGTH: 1161
<212> TYPE: DNA
<213> ORGANISM: Mycobacterium tuberculosis

<400> SEQUENCE: 14

```
aggcgggaat gaacaccgtc acagccgagt ccatcgcgac ctcgagttcg agatcgcgca      60
gcaccaccgt gccggagacg atatccagat cgcgatggaa cgtgatatcc cgcggcccga     120
tgaaggtgtc gtagaagcgg ccgatggcct catgccccac ctgcggctgc gaacccaccg     180
ggtcttcgac ccgcgcgtca ccggtgaaca acccgaccca gccggcgcgg tcgtgcgcgg     240
cggccgcttg cggcgagcgc tccaccgccg ccaacagttc atcccggttc ggcggtgcca     300
tcaggagctg caaaccaact cgacgctggc ggtgcgcatc tcctccagcg cggcgacggt     360
ggtatcggcc gacacaccccg ctgtcaggtc caccagcacc ctggtggcca agccattgcg     420
taccgcgtcc tcggccgtct ggcgcacaca atgatcggtg caataccga ccacatcgac      480
ctcatcgacg ccgcgttgcc gcagccaatt cagcagtggc gtgccgttct cgtcgactcc     540
ttcgaagccg ctgtacgctc cggtgtaggc acccttgtag aacaccgcct cgattgccga     600
cgtgtccaga ctgggatgga agtccgcgcc gggagtaccg ctgacgcaat gcggtggcca     660
cgacgaggaa tagtccggtg tgccggagaa gtggtcaccc gggtcgatgt ggaagtcctt     720
ggttgccacg acgtgatggt agtccgccgc ttcggccagg tagtcgctga tggcgcgggc     780
cagcgcggcg ccaccggtta ccgccagcga gccacccctcg cagaagtcgt tctgcacgtc     840
gacgatgatc aacgcccgca tacgtccacc atacgttcgg gcgactgccc gggcagtttg     900
cctaccgacg cggcagccac agatataggg tccatgacgc cgcgacgatc gcgaacatga     960
ccagctgagc ggcggccacc caaccggcgg gatagatcac gccggtgatg tagtgagcga    1020
caaatccgtc cggtgacaga ggtgtcatcg cggccttggt gcgagcccag cgctccaccc    1080
aggtcagcgg gcagtcgacc cgcttagcgg cgatgccgat ccccatatc accgccggaa     1140
catgcagcca catcgtgcgt c                                              1161
```

<210> SEQ ID NO 15
<211> LENGTH: 1161
<212> TYPE: DNA
<213> ORGANISM: Mycobacterium tuberculosis

<400> SEQUENCE: 15

```
gacgcacgat gtggctgcat gttccggcgg tgatatgggg gatcggcatc gccgctaagc      60
gggtcgactg cccgctgacc tgggtggagc gctgggctcg caccaaggcc gcgatgacac     120
ctctgtcacc ggacggattt gtcgctcact acatcaccgg cgtgatctat cccgccggtt     180
gggtggccgc cgctcagctg gtcatgttcg cgatcgtcgc ggcgtcatgg accctatatc     240
tgtggctgcc gcgtcggtag gcaaactgcc cgggcagtcg cccgaacgta tggtggacgt     300
atgcgggcgt tgatcatcgt cgacgtgcag aacgacttct gcgagggtgg ctcgctggcg     360
gtaaccggtg gcgccgcgct ggcccgcgcc atcagcgact acctggccga agcggcggac     420
taccatcacg tcgtggcaac caaggacttc cacatcgacc cgggtgacca cttctccggc     480
acaccggact attcctcgtc gtggccaccg cattgcgtca gcggtactcc cggcgcggac     540
ttccatccca gtctgacac gtcggcaatc gaggcggtgt tctacaaggg tgcctacacc      600
ggagcgtaca gcggcttcga aggagtcgac gagaacggca cgccactgct gaattggctg     660
```

-continued

```
cggcaacgcg gcgtcgatga ggtcgatgtg gtcggtattg ccaccgatca ttgtgtgcgc    720
cagacggccg aggacgcggt acgcaatggc ttggccacca gggtgctggt ggacctgaca    780
gcgggtgtgt cggccgatac caccgtcgcc gcgctggagg agatgcgcac cgccagcgtc    840
gagttggttt gcagctcctg atggcaccgc cgaaccggga tgaactgttg gcggcggtgg    900
agcgctcgcc gcaagcggcc gccgcgcacg accgcgccgg ctgggtcggg ttgttcaccg    960
gtgacgcgcg ggtcgaagac ccggtgggtt cgcagccgca ggtggggcat gaggccatcg    1020
gccgcttcta cgacaccttc atcgggccgc gggatatcac gttccatcgc gatctggata    1080
tcgtctccgg cacggtggtg ctgcgcgatc tcgaactcga ggtcgcgatg gactcggctg    1140
tgacggtgtt cattcccgcc t                                              1161
```

<210> SEQ ID NO 16
<211> LENGTH: 186
<212> TYPE: PRT
<213> ORGANISM: Mycobacterium tuberculosis

<400> SEQUENCE: 16

```
Met Arg Ala Leu Ile Ile Val Asp Val Gln Asn Asp Phe Cys Glu Gly
1               5                   10                  15

Gly Ser Leu Ala Val Thr Gly Gly Ala Ala Leu Ala Arg Ala Ile Ser
            20                  25                  30

Asp Tyr Leu Ala Glu Ala Ala Asp Tyr His His Val Ala Thr Lys
        35                  40                  45

Asp Phe His Ile Asp Pro Gly Asp His Phe Ser Gly Thr Pro Asp Tyr
    50                  55                  60

Ser Ser Ser Trp Pro Pro His Cys Val Ser Gly Thr Pro Gly Ala Asp
65                  70                  75                  80

Phe His Pro Ser Leu Asp Thr Ser Ala Ile Glu Ala Val Phe Tyr Lys
                85                  90                  95

Gly Ala Tyr Thr Gly Ala Tyr Ser Gly Phe Glu Gly Val Asp Glu Asn
            100                 105                 110

Gly Thr Pro Leu Leu Asn Trp Leu Arg Gln Arg Gly Val Asp Glu Val
        115                 120                 125

Asp Val Val Gly Ile Ala Thr Asp His Cys Val Arg Gln Thr Ala Glu
    130                 135                 140

Asp Ala Val Arg Asn Gly Leu Ala Thr Arg Val Leu Val Asp Leu Thr
145                 150                 155                 160

Ala Gly Val Ser Ala Asp Thr Thr Val Ala Leu Glu Glu Met Arg
                165                 170                 175

Thr Ala Ser Val Glu Leu Val Cys Ser Ser
            180                 185
```

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17

```
tcatggaccc tatatctgtg                                                20
```

<210> SEQ ID NO 18
<211> LENGTH: 20

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
atgaactgtt ggcggcggtg                                                       20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
acggatttgt cgctcactac                                                       20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
atctggatat cgtctccggc                                                       20

<210> SEQ ID NO 21
<211> LENGTH: 1737
<212> TYPE: DNA
<213> ORGANISM: Mycobacterium tuberculosis

<400> SEQUENCE: 21
ggccatgctc ttgatgcccc gttgtcgggg gcgtggccgt tgttttgtc  aggatatttc           60 taaataccttt tggctccctt ttccaaaggg agtgtttggg ttttgtttgg agagtttgat          120
cctggctcag gacgaacgct ggcggcgtgc ttaacacatg caagtcgaac ggaaaggtct          180
cttcggagat actcgagtgg cgaacgggtg agtaacacgt gggtgatctg ccctgcactt          240
cgggataagc ctgggaaact gggtctaata ccggatagga ccacgggatg catgtcttgt          300
ggtggaaagc gctttagcgg tgtgggatga gcccgcggcc tatcagcttg ttggtggggt          360
gacggcctac caaggcgacg acgggtagcc ggcctgagag ggtgtccggc cacactggga          420
ctgagatacg gcccagactc ctacggggagg cagcagtggg gaatattgca caatgggcgc         480
aagcctgatg cagcgacgcc gcgtggggga tgacggcctt cgggttgtaa acctctttca          540
ccatcgacga aggtccgggt tctctcggat tgacggtagg tggagaagaa gcaccggcca          600
actacgtgcc agcagccgcg gtaatacgta gggtgcgagc gttgtccgga attactgggc          660
gtaaagagct cgtaggtggt tgtcgcgtt gttcgtgaaa tctcacggct taactgtgag           720
cgtgcgggcg atacgggcag actagagtac tgcaggggag actggaattc ctggtgtagc          780
ggtggaatgc gcagatatca ggaggaacac cggtggcgaa ggcgggtctc tgggcagtaa          840
ctgacgctga ggagcgaaag cgtggggagc gaacaggatt agataccctg gtagtccacg          900
ccgtaaacgg tgggtactag gtgtgggttt ccttccttgg gatccgtgcc gtagctaacg          960
cattaagtac cccgcctggg gagtacggcc gcaaggctaa aactcaaagg aattgacggg         1020
ggcccgcaca agcggcggag catgtggatt aattcgatgc aacgcgaaga accttacctg         1080
```

```
ggtttgacat gcacaggacg cgtctagaga taggcgttcc cttgtggcct gtgtgcaggt    1140
ggtgcatggc tgtcgtcagc tcgtgtcgtg agatgttggg ttaagtcccg caacgagcgc    1200 aaccettgtc tcatgttgcc agcacgtaat ggtggggact cgtgagagac tgccggggtc    1260
aactcggagg aaggtgggga tgacgtcaag tcatcatgcc ccttatgtcc agggcttcac    1320
acatgctaca atggccggta caaagggctg cgatgccgcg aggttaagcg aatccttaaa    1380
agccggtctc agttcggatc ggggtctgca actcgacccc gtgaagtcgg agtcgctagt    1440
aatcgcagat cagcaacgct gcggtgaata cgttcccggg ccttgtacac accgcccgtc    1500
acgtcatgaa agtcggtaac acccgaagcc agtggcctaa ccctcgggag ggagctgtcg    1560
aaggtgggat cggcgattgg gacgaagtcg taacaaggta gccgtaccgg aaggtgcggc    1620
tggatcacct cctttctaag gagcaccacg aaaacgcccc aactggtggg gcgtaggccg    1680
tgaggggttc ttgtctgtag tgggcgagag ccgggtgcat gacaacaaag ttggcca       1737

<210> SEQ ID NO 22
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
tggccgtttg ttttgtcagg at                                               22

<210> SEQ ID NO 23
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
tacagacaag aaccectcac gg                                               22

<210> SEQ ID NO 24
<211> LENGTH: 1773
<212> TYPE: DNA
<213> ORGANISM: Mycobacterium tuberculosis

<400> SEQUENCE: 24
gatccggaca gatcgttcgc cggccgaaac cgacaaaatt atcgcggcga acgggcccgt      60
gggcaccgct cctctaaggg ctctcgttgg tcgcatgaag tgctggaagg atgcatcttg     120
gcagattccc gccagagcaa aacagccgct agtcctagtc cgagtcgccc gcaaagttcc     180
tcgaataact ccgtacccgg agcgccaaac cgggtctcct tcgctaagct gcgcgaacca     240
cttgaggttc cgggactcct tgacgtccag accgattcgt tcgagtggct gatcggttcg     300
ccgcgctggc gcgaatccgc cgccgagcgg ggtgatgtca acccagtggg tggcctggaa     360
gaggtgctct acgagctgtc tccgatcgag gacttctccg gtcgatgtc gttgtcgttc      420 tctgaccctc gtttcgacga tgtcaaggca cccgtcgacg agtgcaaaga caaggacatg     480
acgtacgcgg ctccactgtt cgtcaccgcc gagttcatca acaacaacac cggtgagatc     540
aagagtcaga cggtgttcat gggtgacttc ccgatgatga ccgagaaggg cacgttcatc     600
atcaacggga ccgagcgtgt ggtggtcagc cagctggtgc ggtcgccegg ggtgtacttc     660
```

```
gacgagacca ttgacaagtc caccgacaag acgctgcaca gcgtcaaggt gatcccgagc      720
cgcggcgcgt ggctcgagtt tgacgtcgac aagcgcgaca ccgtcggcgt gcgcatcgac      780
cgcaaacgcc ggcaaccggt caccgtgctg ctcaaggcgc tgggctggac cagcgagcag      840
attgtcgagc ggttcgggtt ctccgagatc atgcgatcga cgctggagaa ggacaacacc      900
gtcggcaccg acgaggcgct gttggacatc taccgcaagc tgcgtccggg cgagcccccg      960
accaaagagt cagcgcagac gctgttggaa aacttgttct tcaaggagaa gcgctacgac     1020
ctggcccgcg tcggtcgcta aaggtcaac aagaagctcg ggctgcatgt cggcgagccc     1080
atcacgtcgt cgacgctgac cgaagaagac gtcgtggcca ccatcgaata tctggtccgc     1140
ttgcacgagg gtcagaccac gatgaccgtt ccgggcggcg tcgaggtgcc ggtggaaacc     1200
gacgacatcg accacttcgg caaccgccgc ctgcgtacgg tcggcgagct gatccaaaac     1260
cagatccggg tcggcatgtc gcggatggag cgggtggtcc gggagcggat gaccacccag     1320
gacgtggagg cgatcacacc gcagacgttg atcaacatcc ggccggtggt cgccgcgatc     1380
aaggagttct tcggcaccag ccagctgagc caattcatgg accagaacaa cccgctgtcg     1440
gggttgaccc acaagcgccg actgtcggcg ctggggcccg gcggtctgtc acgtgagcgt     1500
gccgggctgg aggtccgcga cgtgcacccg tcgcactacg gccggatgtg cccgatcgaa     1560 accctgagg ggcccaacat cggtctgatc ggctcgctgt cggtgtacgc gcgggtcaac     1620
ccgttcgggt tcatcgaaac gccgtaccgc aaggtggtcg acggcgtggt tagcgacgag     1680
atcgtgtacc tgaccgccga cgaggaggac cgccacgtgg tggcacaggc caattcgccg     1740
atcgatgcgg acggtcgctt cgtcgagccg cgc                                  1773
```

<210> SEQ ID NO 25
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
accgacaaaa ttatcgcggc ga                                                22

<210> SEQ ID NO 26
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
atcgatcggc gaattggcct gt                                                22

<210> SEQ ID NO 27
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
tcgccgcgat caaggagt                                                     18

<210> SEQ ID NO 28

```
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
tggaggtccg cgacgtgca                                                    19

<210> SEQ ID NO 29
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
aatatctggt ccgcttgcac ga                                                22

<210> SEQ ID NO 30
<211> LENGTH: 2717
<212> TYPE: DNA
<213> ORGANISM: Mycobacterium tuberculosis

<400> SEQUENCE: 30
gacgtcgacg cgcggcgcag ctttatcacc cgcaacgcca aggatgttcg gttcctggat      60
gtctaacgca accctgcgtt cgattgcaaa cgaggaatag atgacagaca cgacgttgcc     120
gcctgacgac tcgctcgacc ggatcgaacc ggttgacatc gagcaggaga tgcagcgcag     180
ctacatcgac tatgcgatga gcgtgatcgt cggccgcgcg ctgccggagg tgcgcgacgg     240
gctcaagccc gtgcatcgcc gggtgctcta tgcaatgttc gattccggct ccgcccgga     300 ccgcagccac gccaagtcgg cccggtcggt tgccgagacc atgggcaact accacccgca     360
cggcgacgcg tcgatctacg acagcctggt gcgcatggcc cagccctggt cgctgcgcta     420
cccgctggtg gacggccagg gcaacttcgg ctcgccaggc aatgacccac cggcggcgat     480
gaggtacacc gaagcccggc tgaccccgtt ggcgatggag atgctgaggg aaatcgacga     540
ggagacagtc gatttcatcc ctaactacga cggccgggtg caagagccga cggtgctacc     600
cagccggttc cccaacctgc tggccaacgg gtcaggcggc atcgcggtcg gcatggcaac     660
caatatcccg ccgcacaacc tgcgtgagct ggccgacgcg gtgttctggg cgctggagaa     720
tcacgacgcc gacgaagagg agaccctggc cgcggtcatg gggcgggtta aaggcccgga     780
cttcccgacc gccggactga tcgtcggatc ccagggcacc gctgatgcct acaaaactgg     840
ccgcggctcc attcgaatgc gcggagttgt tgaggtagaa gaggattccc gcggtcgtac     900
ctcgctggtg atcaccgagt tgccgtatca ggtcaaccac gacaacttca tcacttcgat     960
cgccgaacag gtccgagacg gcaagctggc cggcatttcc aacattgagg accagtctag    1020
cgatcgggtc ggtttacgca tcgtcatcga gatcaagcgc gatgcggtgg ccaaggtggt    1080
gatcaataac ctttacaagc acacccagct gcagaccagc tttggcgcca acatgctagc    1140
gatcgtcgac ggggtgccgc gcacgctgcg gctggaccag ctgatccgct attacgttga    1200
ccaccaactc gacgtcattg tgcggcgcac cacctaccgg ctgcgcaagg caaacgagcg    1260
agcccacatt ctgcgcggcc tggttaaagc gctcgacgcg ctggacgagg tcattgcact    1320
gatcggggcg tcgagaccg tcgatatcgc ccgggccgga ctgatcgagc tgctcgacat    1380
cgacgagatc caggcccagg caatcctgga catgcagttg cggcgcctgg ccgcactgga    1440
```

```
acgccagcgc atcatcgacg acctggccaa aatcgaggcc gagatcgccg atctggaaga   1500
catcctggca aaacccgagc ggcagcgtgg gatcgtgcgc gacgaactcg ccgaaatcgt   1560
ggacaggcac ggcgacgacc ggcgtacccg gatcatcgcg gccgacggag acgtcagcga   1620
cgaggatttg atcgcccgcg aggacgtcgt tgtcactatc accgaaacgg gatacgccaa   1680
gcgcaccaag accgatctgt atcgcagcca gaaacgcggc ggcaagggcg tgcagggtgc   1740
ggggttgaag caggacgaca tcgtcgcgca cttcttcgtg tgctccaccc acgatttgat   1800
cctgttcttc accacccagg gacgggttta tcgggccaag gcctacgact tgcccgaggc   1860
ctcccggacg gcgcgcgggc agcacgtggc caacctgtta gccttccagc ccgaggaacg   1920
catcgcccag gtcatccaga ttcgcggcta caccgacgcc ccgtacctgg tgctggccac   1980
tcgcaacggg ctggtgaaaa agtccaagct gaccgacttc gactccaatc gctcgggcgg   2040
aatcgtggcg gtcaacctgc gcgacaacga cgagctggtc ggtgcggtgc tgtgttcggc   2100
cggcgacgac ctgctgctgg tctcggccaa cgggcagtcc atcaggttct cggcgaccga   2160
cgaggcgctg cggccaatgg gtcgtgccac ctcgggtgtg cagggcatgc ggttcaatat   2220
cgacgaccgt ctgctgtcgc tgaacgtcgt gcgtgaaggc acctatctgc tggtggcgac   2280
gtcagggggc tatgcgaaac gtaccgcgat cgaggaatac ccggtacagg gccgcggcgg   2340
taaaggtgtg ctgacggtca tgtacgaccg ccggcgcggc aggttggttg gggcgttgat   2400
tgtcgacgac gacagcgagc tgtatgccgt cacttccggc ggtggcgtga tccgcaccgc   2460
ggcacgccag gttcgcaagg cgggacggca gaccaagggt gttcggttga tgaatctggg   2520
cgagggcgac acactgttgg ccatcgcgcg caacgccgaa gaaagtggcg acgataatgc   2580
cgtggacgcc aacggcgcag accagacggg caattaatca ggctcgcccg acgacgatgc   2640
ggatcgcgta gcgatctgag gaggaatcgg gcagctaggc tcggcagccg ggtacgagtg   2700
ttaggagtcg gggtgac                                                 2717
```

<210> SEQ ID NO 31
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
ctaacgcaac cctgcgttcg at                                             22

<210> SEQ ID NO 32
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
attcctcctc agatcgctac g                                              21

<210> SEQ ID NO 33
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33

```
cgtcgtagtt agggatgaaa tc                                              22
```

<210> SEQ ID NO 34
<211> LENGTH: 2640
<212> TYPE: DNA
<213> ORGANISM: Mycobacterium tuberculosis

<400> SEQUENCE: 34

```
gtcttgcggg gttatcgccg atgtcgactg tgctgttggc gaggcaccct gtctgacggc      60
ctcggaccat aacggcttcc tgttggacga ggcggaggtc atctactggg tctatgtcc     120
tgattgttcg atatccgaca cttcgcgatc acatccgtga tcacagcccg ataacaccaa    180
ctcctggaag gaatgctgtg cccgagcaac acccacccat tacagaaacc accaccggag    240
ccgctagcaa cggctgtccc gtcgtgggtc atatgaaata ccccgtcgag ggcggcggaa    300
accaggactg tggcccaac cggctcaatc tgaaggtact gcaccaaaac ccggccgtcg     360
ctgacccgat gggtgcggcg ttcgactatg ccgcggaggt cgcgaccatc gacgttgacg    420
ccctgacgcg ggacatcgag gaagtgatga ccacctcgca gccgtggtgg cccgccgact    480
acggccacta cgggccgctg tttatccgga tggcgtggca cgctgccggc acctaccgca    540
tccacgacgg ccgcggcggc gccggggcg gcatgcagcg gttcgcgccg cttaacagct     600
ggcccgacaa cgccagcttg gacaaggcgc gccggctgct gtggccggtc aagaagaagt    660
acggcaagaa gctctcatgg gcggacctga ttgttttcgc cggcaactgc gcgctggaat    720
cgatgggctt caagacgttc gggttcggct tcggccgggt cgaccagtgg gagcccgatg    780
aggtctattg gggcaaggaa ccacctggc tcggcgatga cgttacagc ggtaagcggg      840
atctggagaa cccgctggcc gcggtgcaga tggggctgat ctacgtgaac ccggaggggc    900
cgaacggcaa cccggacccc atggccgcgg cgtcgacat cgcgagacg tttcggcgca     960
tggccatgaa cgacgtcgaa acagcggcgc tgatcgtcgg cggtcacact ttcggtaaga   1020
cccatggcgc cggcccggcc gatctggtcg gccccgaacc cgaggctgct ccgctggagc   1080
agatgggctt gggctggaag agctcgtatg caccggaaac cggtaaggac gcgatcacca   1140
gcggcatcga ggtcgtatgg acgaacaccc cgacgaaatg gacaacagt ttcctcgaga    1200
tcctgtacgc ctacgagtgg gagctgacga agagccctgc tggcgcttgg caatacaccg   1260
ccaaggacgg cgccggtgcc ggcaccatcc cggacccgtt cggcgggcca gggcgctccc   1320
cgacgatgct ggccactgac ctctcgctgc gggtggatcc gatctatgag cggatcacgc   1380
gtcgctggct ggaacacccc gaggaattgg ccgacgagtt cgccaaggcc tggtacaagc   1440
tgatccaccg agacatgggt cccgttgcga gataccttgg gccgctggtc cccaagcaga   1500
ccctgctgtg gcaggatccg gtccctgcgg tcagccacga cctcgtcggc gaagccgaga   1560
ttgccagcct taagagccag atccgggcat cgggattgac tgtctcacag ctagtttcga   1620
ccgcatgggc ggcggcgtcg tcgttccgtg gtagcgacaa gcgcggcggc gccaacggtg   1680
gtcgcatccg cctgcagcca caagtcgggt gggaggtcaa cgaccccgac ggggatctgc   1740
gcaaggtcat tcgcaccctg gaagagatcc aggagtcatt caactccgcg cgccggggaa   1800
acatcaaagt gtccttcgcc gacctcgtcg tgctcggtgg ctgtgccgcc atagagaaag   1860
cagcaaaggc ggctggccac aacatcacgg tgcccttcac cccgggccgc acggatgcgt   1920
cgcaggaaca aaccgacgtg gaatcctttg ccgtgctgga gcccaaggca gatggcttcc   1980
```

-continued

```
gaaactacct cggaaagggc aacccgttgc cggccgagta catgctgctc gacaaggcga    2040
acctgcttac gctcagtgcc cctgagatga cggtgctggt aggtggcctg cgcgtcctcg    2100
gcgcaaacta caagcgctta ccgctgggcg tgttcaccga ggcctccgag tcactgacca    2160
acgacttctt cgtgaacctg ctcgacatgg gtatcacctg ggagccctcg ccagcagatg    2220
acgggaccta ccagggcaag gatggcagtg gcaaggtgaa gtggaccggc agccgcgtgg    2280
acctggtctt cgggtccaac tcggagttgc gggcgcttgt cgaggtctat ggcgccgatg    2340
acgcgcagcc gaagttcgtg caggacttcg tcgctgcctg ggacaaggtg atgaacctcg    2400
acaggttcga cgtgcgctga ttcggggttga tcggccctgc ccgccgatca accacaaccc    2460
gccgcagcac cccgcgagct gaccggctcg cggggtgctg gtgtttgccc ggcgcgattt    2520
gtcagacccc gcgtgcatgg tggtcgcagg cacgacgaga cggggatgac gagacgggga    2580
tgaggagaaa gggcgccgaa atgtgctgga tgtgcgatca cccggaagcc accgccgagg    2640
```

<210> SEQ ID NO 35
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
tcgcgatcac atccgtgatc ac                                              22

<210> SEQ ID NO 36
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
atgcacgcgg ggtctgacaa at                                              22

<210> SEQ ID NO 37
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
acaccaactc ctggaaggaa t                                               21

<210> SEQ ID NO 38
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
ttacagcggt aagcgggatc t                                               21

<210> SEQ ID NO 39
<211> LENGTH: 22
<212> TYPE: DNA
<213> ORGANISM: Artificial Sequence -continued

```
<220> FEATURE:
<223> OTHER INFORMATION: Description of Artificial Sequence: Synthetic
      primer

<400> SEQUENCE: 39
ttggcgaact cgtcggccaa tt                                              22

<210> SEQ ID NO 40
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
attatattca gtatggaaag aa                                              22

<210> SEQ ID NO 41
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
atatatccac agcttgttc                                                  19

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
gatccactag catctttatt                                                 20

<210> SEQ ID NO 43
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
gtacgtctct catttgtt                                                   18

<210> SEQ ID NO 44
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
aaggcatttt cagaaagat                                                  19

<210> SEQ ID NO 45
<211> LENGTH: 21
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 45
gtcgttttta aactattcag c                                              21

<210> SEQ ID NO 46
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
accatttgaa tggatgtc                                                  18

<210> SEQ ID NO 47
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
ttgattcttt gtgatgtatg t                                              21

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
aatgatgact aattcacaag                                                20

<210> SEQ ID NO 49
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
ataattctca tccatcagc                                                 19

<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
aaatacacca agacaacata                                                20

<210> SEQ ID NO 51
<211> LENGTH: 19
<212> TYPE: DNA
<213> ORGANISM: Artificial Sequence
<220> FEATURE:
<223> OTHER INFORMATION: Description of Artificial Sequence: Synthetic
```

```
                        primer

<400> SEQUENCE: 51
catgaaggac aagctaaat                                                19

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
attttgaatg gatgtcaatc                                               20

<210> SEQ ID NO 53
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
gtgattgtga agaaaagct                                                19

<210> SEQ ID NO 54
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
ctgattcgaa atggaaga                                                 18

<210> SEQ ID NO 55
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
cgtgtggttt gactatat                                                 18

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
gatcaagtgc ataaaaacat                                               20

<210> SEQ ID NO 57
<211> LENGTH: 19
<212> TYPE: DNA
<213> ORGANISM: Artificial Sequence
<220> FEATURE:
<223> OTHER INFORMATION: Description of Artificial Sequence: Synthetic
      primer
```

-continued

<400> SEQUENCE: 57
atagagtcct acagacttt                                                   19

<210> SEQ ID NO 58
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
tgacgaacct gaattaag                                                    18

<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
gtacggataa caaatagtag                                                  20

<210> SEQ ID NO 60
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
taattctatt aaccatgaag ac                                               22

<210> SEQ ID NO 61
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
gcatctgatc tcattattg                                                   19

<210> SEQ ID NO 62
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
catacttttg attaacagca                                                  20

<210> SEQ ID NO 63
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
ttaatgcact caaatgca                                                 18

<210> SEQ ID NO 64
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
aataatcact cactgagtg                                                19

<210> SEQ ID NO 65
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
aatatgagat cttcgatctc                                               20

<210> SEQ ID NO 66
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
acaagaagtg cttatgag                                                 18

<210> SEQ ID NO 67
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
ttccttaatt gtcgtactc                                                19

<210> SEQ ID NO 68
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
ctgagtgaca tcaaaatca                                                19

<210> SEQ ID NO 69
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69

```
gcagctgttt gaaattttc                                              19

<210> SEQ ID NO 70
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
aagatgaatc caaaccaa                                               18

<210> SEQ ID NO 71
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
gtatcagctt ttcctgaa                                               18

<210> SEQ ID NO 72
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
gatagtgttg tttcatgg                                               18

<210> SEQ ID NO 73
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
ctaaaattgc gaaagcttat a                                           21

<210> SEQ ID NO 74
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
atattgaaag atgagcctt                                              19

<210> SEQ ID NO 75
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
```

```
tagtttttta ctccaactct a                                              21
```

<210> SEQ ID NO 76
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76

```
acaaagacat aatggattct                                                20
```

<210> SEQ ID NO 77
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77

```
ggtgttttttt atcatcaaat aag                                           23
```

<210> SEQ ID NO 78
<211> LENGTH: 960
<212> TYPE: DNA
<213> ORGANISM: Mycobacterium tuberculosis

<400> SEQUENCE: 78

```
gacggatttg tcgctcacta catcaccggc gtgatctatc ccgccggttg ggtggccgcc    60
gctcagctgg tcatgttcgc gatcgtcgcg gcgtcatgga ccctatatct gtggctgccg   120
cgtcggtagg caaactgccc gggcagtcgc ccgaacgtat ggtggacgta tgcgggcgtt   180
gatcatcgtc gacgtgcaga acgacttctg cgagggtggc tcgctggcgg taaccggtgg   240
cgccgcgctg gcccgcgcca tcagcgacta cctggccgaa gcggcggact accatcacgt   300
cgtggcaacc aaggacttcc acatcgaccc gggtgaccac ttctccggca caccggacta   360
ttcctcgtcg tggccaccgc attgcgtcag cggtactccc ggcgcggact tccatcccag   420
tctggacacg tcggcaatcg aggcggtgtt ctacaagggt gcctacaccg agcgtacag    480
cggcttcgaa ggagtcgacg agaacggcac gccactgctg aattggctgc ggcaacgcgg   540
cgtcgatgag gtcgatgtgg tcggtattgc caccgatcat tgtgtgcgcc agacggccga   600
ggacgcggta cgcaatggct tggccaccag ggtgctggtg gacctgacag cgggtgtgtc   660
ggccgatacc accgtcgccg cgctggagga gatgcgcacc gccagcgtcg agttggtttg   720
cagctcctga tggcaccgcc gaaccgggat gaactgttgg cggcggtgga gcgctcgccg   780
caagcggccg ccgcgcacga ccgcgccggc tgggtcgggt tgttcaccgg tgacgcgcgg   840
gtcgaagacc cggtgggttc gcagccgcag gtggggcatg aggccatcgg ccgcttctac   900
gacaccttca tcgggccgcg ggatatcacg ttccatcgcg atctggatat cgtctccggc   960
```

<210> SEQ ID NO 79
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79

```
gacggatttg tcgctcac                                                  18

<210> SEQ ID NO 80
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
agccaccctc gcagaa                                                    16

<210> SEQ ID NO 81
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
catcgtcgac gtgcagaa                                                  18

<210> SEQ ID NO 82
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
tgtccagact gggatggaa                                                 19

<210> SEQ ID NO 83
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
attgcgtcag cggtact                                                   17

<210> SEQ ID NO 84
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
tggccaagcc attgcgta                                                  18

<210> SEQ ID NO 85
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
atcattgtgt gcgccaga                                                  18
```

-continued

```
<210> SEQ ID NO 86
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
caacagttca tcccggtt                                                   18

<210> SEQ ID NO 87
<211> LENGTH: 221
<212> TYPE: DNA
<213> ORGANISM: Mycobacterium tuberculosis

<400> SEQUENCE: 87
gacggatttg tcgctcacta catcaccggc gtgatctatc ccgccggttg ggtggccgcc     60
gctcagctgg tcatgttcgc gatcgtcgcg cgtcatgga ccctatatct gtggctgccg    120
cgtcggtagg caaactgccc gggcagtcgc ccgaacgtat ggtggacgta tgcgggcgtt   180
gatcatcgtc gacgtgcaga acgacttctg cgagggtggc t                        221

<210> SEQ ID NO 88
<211> LENGTH: 245
<212> TYPE: DNA
<213> ORGANISM: Mycobacterium tuberculosis

<400> SEQUENCE: 88
catcgtcgac gtgcagaacg acttctgcga gggtggctcg ctggcggtaa ccggtggcgc     60
cgcgctggcc cgcgccatca gcgactacct ggccgaagcg gcggactacc atcacgtcgt   120
ggcaaccaag gacttccaca tcgacccggg tgaccacttc tccggcacac cggactattc   180
ctcgtcgtgg ccaccgcatt gcgtcagcgg tactcccggc gcggacttcc atcccagtct   240
ggaca                                                                245

<210> SEQ ID NO 89
<211> LENGTH: 246
<212> TYPE: DNA
<213> ORGANISM: Mycobacterium tuberculosis

<400> SEQUENCE: 89
attgcgtcag cggtactccc ggcgcggact ccatcccag tctggacacg tcggcaatcg     60
aggcggtgtt ctacaagggt gcctacaccg gagcgtacag cggcttcgaa ggagtcgacg   120
agaacggcac gccactgctg aattggctgc ggcaacgcgg cgtcgatgag gtcgatgtgg   180
tcggtattgc caccgatcat tgtgtgcgcc agacggccga ggacgcggta cgcaatggct   240
tggcca                                                               246

<210> SEQ ID NO 90
<211> LENGTH: 184
<212> TYPE: DNA
<213> ORGANISM: Mycobacterium tuberculosis

<400> SEQUENCE: 90
atcattgtgt gcgccagacg gccgaggacg cggtacgcaa tggcttggcc accagggtgc     60
tggtggacct gacagcgggt gtgtcggccg ataccaccgt cgccgcgctg gaggagatgc   120
```

```
gcaccgccag cgtcgagttg gtttgcagct cctgatggca ccgccgaacc gggatgaact    180
gttg                                                                 184
```

ION TORRENT GENOMIC SEQUENCING

REFERENCE TO RELATED APPLICATIONS

Fins application claims priority to U.S. Provisional Application No. 61/737,250 entitled "Ion Torrent Genomic Sequencing" filed Dec. 14, 2012, U.S. Provisional Application No. 61/695,960 entitled "Ion Torrent Genomic Sequencing" filed Aug. 31, 2012, U.S. Provisional Application No. 61/646,060 entitled "Drug Susceptibility Determination by Ion Torrent Sequencing" filed May 11, 2012, and U.S. Provisional Application No. 61/644,876 "Drug Susceptibility Determination by Ion Torrent Sequencing" filed May 9, 2012, and the entirety of each of which is specifically incorporated by reference.

SEQUENCE LISTING

The instant application contains a Sequence Listing which has been submitted in ASCII format via EFS-Web and is hereby incorporated by reference in its entirety. Said ASCII copy, created on May 7, 2013, is named 3022.018.US_SL.txt and is 37,929 bytes in size.

BACKGROUND

1. Field of the Invention

This invention is directed to tools, compositions and methods for identifying genetic mutation and mega-bases of nucleic acid information by semi-conductor sequencing and, in particular, to analyzing genes and complete genomes by ion torrent sequencing.

2. Description of the Background

*Mycobacterium tuberculosis* (MTB), the causative agent for tuberculosis, is a highly transmissible bacterial pathogen with significant morbidity and mortality, particularly in HIV infected patients. Since 1997 tuberculosis has remained the leading cause of death in South Africa, a statistic linked to this country's growing HIV epidemic. Moreover, effective treatment measures in patients with active MTB have been exacerbated by increasing cases of multidrug resistance (MDR) and extensively drug-resistant (XDR) clinical isolates.

MDR tuberculosis strains are resistant to the first line antibiotics rifampin (RIF) and isoniazid (INH), while XDR MTB strains are resistant to both RIF and INH as well as any fluoroquinolone and second-line injectable antibiotic drugs (e.g., amikacin, kanamycin or capreomycin). About 6% of all TB cases are MDR strains and South Africa continues to report higher percentages of XDR cases each year. While 7% of patients infected with standard MTB strains succumb to infection, the death rate rises to almost 50% with MDR tuberculosis. The emergence of antibiotic resistant MTB strains underscores an immediate need for rapid and highly accurate diagnosis, particularly in the developing countries of Africa. In addition migratory populations make geographical surveillance and tracking of drug resistance strains more urgent.

Culture-based drug susceptibility testing (DST) for MDR strains is considered the gold-standard, but is time consuming (weeks to months), technically challenging and cost prohibitive, especially in resource limited countries. For example, the BACTEC MGIT 960 (Becton Dickinson Microbiology System, Silver Sparks Nev., USA), is an automated continuously culture-based monitoring system that measures bacterial oxygen consumption and can perform DST using prepared kits which are available for susceptibility of strains to a number of antibiotics. DST results obtained with the BACTEC MGIT 960 yield reliable and reproducible but require handling of viable and potentially infectious cultures, days to weeks or delay until results are available, specialized laboratory accommodations and high costs associated with the instrument and consumables.

In recent years, several nucleic acid based assays for determining MTB drug resistance have been developed. One of the most popular commercially available diagnostic assays is the GenoType MTBDRplus Line Probe Assay (LPA) by Hain LifeScience. This test employs nucleic acid extraction, PCR amplification, probe hybridization and colorimetric visualization on lateral strips via an alkaline phosphatase reaction. LPA has been shown to be sensitive and specific, but there are several drawbacks. Sensitivity of the LPA for all resistance-associated mutations will most likely never reach 100% since many mutations that confer resistance have yet to be discovered. Another inherent limitation of the LPA is an inability to detect sample populations that contain a mixture of resistant and susceptible strains. Strains that harbor substitution mutations that change an amino acid to a previously uncharacterized or unknown mutation not presented on the LPA are not detected. Furthermore, the LPA only allows detection of the most frequent mutations that cause resistance. If a strain were to contain, mutations outside of the targeted mutations, the wild-type banding pattern will appear leading to a false negative (susceptible) result.

Thus, there is a need for a rapid, standardized, cost-effective protocol for full length gene analysis of critical genes such as, for example, genes associated with first and second line drug resistance.

SUMMARY

The present invention overcomes disadvantages associated with current strategies and designs, and hereby provides tools, compositions, and methods for analyzing sequence information of nucleic acids including full-length genes and complete genomes.

One embodiment of the invention is directed to analyzing drug resistance mutations by semi-conductor sequencing and, preferably, ion torrent sequencing. Nucleic acid segments containing a gene of interest are amplified by PCR and the amplified products are processed and subsequently analyzed by sequencing. Sequencing is preferably by Ion Torrent, or Next-Generation sequencers including the Ion Torrent Personal Genome Machine (PGM). Preferably, the amplification products represent a common full-length, or multiple overlapping pieces of genes of a number of species, strains and/or serotypes of organisms. The amplified products are sequenced and mutations identified and mapped. Mapping identifies both known and previously unknown mutations and is useful to track the progress and movement of drug resistance across a population. Preferably, the invention analyzes nucleic acids of pathogens such as, for example, virus, bacteria or parasites. Preferably the viral pathogens are the causative agents of influenza or HIV and the bacterial pathogens are the causative agents of tuberculosis. Ion torrent sequencing of the nucleic acid segments provides enhanced sequencing for rapid, efficient, cost-effective protocol for full length gene analysis. Drug resistance and other mutations are immediately determined.

Another embodiment of the invention is directed to tools, compositions and methods for performing semi-conductor sequencing, preferably ion torrent sequencing, on complete genomes. The invention comprises obtaining a DNA sequence of an organism of interest and performing polymerase chain reaction analysis using multiple pairs of nucleic acid primers. Each pair of primers is designed to simultaneously amplify overlapping segments of the genome under similar PCR conditions. Preferred primers possess similar GC content and overall size. A single PCR amplification of the genome produces hundreds of amplification products whose sequences include the full-length gene, large gene and noncoding segments or the entire genome of the organism. These products are analyzed, preferably by ion torrent sequencing, and the sequences matched to create a sequence map of the entire genome.

Another embodiment of the invention is directed to methods of identifying a sequence motif in the genome of a microorganism that confers resistance to an antimicrobial compound, comprising: providing multiple nucleic acid samples obtained from multiple different strains or serotypes of the microorganism; amplifying the sequences of the multiple nucleic acid samples by a polymerase chain reaction; obtaining sequence information of the amplified sequences by ion torrent sequencing; identifying a polymorphism in the genome of at least one microorganism strain or serotype from the sequence information obtained; and correlating the polymorphism identified with a phenotype or genome location of the at least one microorganism strain or serotype to identify the sequence motif that confers resistance to the antimicrobial compound. Preferably, the microorganism is a virus, a bacterium, a fungus or a parasite, and the virus is influenza virus and the bacterium is *Mycobacterium tuberculosis*. Preferably, the nucleic acid samples are provided in an aqueous molecular transport medium that contains a chaotrope, a detergent, a reducing agent, a chelator, a buffer, and an alcohol, together present in an amount sufficient to lyse cells, denature proteins, inactivate nucleases, kill pathogens, and not degrade nucleic acid. Preferably, amplifying is performed in a one step polymerase chain reaction utilizing a primer pair that amplifies a gene or nucleic acid segment associated with resistance to an antimicrobial compound, and the polymerase chain reaction is carried out in an aqueous mix comprising: a heat-stable polymerase; a mix of deoxynucleotide tri phosphates comprising about equivalent amounts of dATP, dCTP, dGTP and dTTP, a chelating agent, an osmolarity agent, an albumin, a magnesium salt; and a buffer. Preferably the antimicrobial compound is an antibiotic.

Another embodiment of the invention is directed to methods of treating a disease or disorder caused by the at least one microorganism strain or serotype with the antimicrobial compound identified by the methods of the invention.

Another embodiment of the invention is directed to methods for determining a complete sequence of a genome of an microorganism comprising: producing a series of amplicons by performing a single polymerase chain reaction (PCR) of the genome in an aqueous mixture containing a heat-stable polymerase; a mix of deoxynucleotide tri phosphates comprising about equivalent amounts of dATP, dCTP, dGTP and dTTP; a chelating agent; a salt; a buffer; a stabilizing agent; and a plurality of primer pairs wherein each primer of the plurality of primer pairs has a similar annealing temperatures; sequencing each of the series of amplicons produced by semi-conductor sequencing, and correlating the sequences of the amplicons and constructing the complete sequence of the genome. Preferably, each of the primers of the multiple primer pairs comprise primers that are from 15 to 25 nucleic acids in length and each has a GC content of about 25-50%. Preferably, each primer pair is designed to PCR amplify an amplicon, and the collection of amplicons that are PCR amplified encompass overlapping segment of the complete genome sequence. Preferably, the plurality of primer pairs hybridize to the genome and are spaced along the genome at about every 500 to 2,000 nucleotides. Preferably, the microorganism is a virus, a bacterium, a fungus, a parasite or a cell, and the virus is influenza virus and the bacterium is *Mycobacterium tuberculosis*.

Another embodiment of the invention is directed to methods for determining the sequence of a nucleic acid segment in one step comprising: performing a polymerase chain reaction on the nucleic acid segment to produce a series of amplicons, wherein the PCR comprises: a heat-stable polymerase; a mix of deoxynucleotide tri phosphates comprising about equivalent amounts of dATP, dCTP, dGTP and dTTP; a chelating agent; a salt; a buffer; a stabilizing agent; and a plurality of primer pairs wherein each primer of the plurality of primer pairs has an annealing temperature within 5° C.; sequencing each of the series of amplicons produced by semi-conductor sequencing, and correlating the sequences of the amplicons and constructing the sequence of the nucleic acid segment. Preferably the nucleic acid segment is 1 Mb or greater in length, more preferably greater 2 or more Mb in length, more preferably 5 or more Mb in length and more preferably 10 or more Mb in length. Preferably, each of the primers of the multiple primer pairs is of from 16 to 24 nucleotides in length, has a GC content of about 28-35%, and has an annealing temperature of within 3° C. of each other primer. Preferably, each primer pair is designed to PCR amplify an amplicon representing a portion of the sequence of the nucleic acid segment, and the collection of amplicons that are PCR amplified represent overlapping portions of the complete sequence of the segment. Preferably, the plurality of primer pairs hybridizes to the segment at a spacing of about 800 to 1,200 nucleotides in length.

Another embodiment of the invention is directed to mixtures comprising multiple pairs of nucleic acid primers wherein, upon subjecting the collection to a polymerase chain reaction in association with a nucleic acid segment, the collection of primer pairs generates a collection of amplicons, wherein each amplicon is about 500 to 2,000 nucleotides in length, such that the entire sequence of the segment is represented in the resulting collection of amplicons. Preferably, each primer of the collection of primer pairs is about 15 to 25 nucleotides in length, has a GC content of about 25-45%, and an annealing temperature within 3° C. of each other primer, and each primer of the collection of primer pairs contains a sequence that hybridizes to the genome of the same microorganism. Preferably, the microorganism is a virus, a bacterium, a parasite, or a fungus. Preferably, the mixture contains a heat-stable polymerase; a mix of deoxynucleotide tri phosphates comprising about equivalent amounts of dATP, dCTP, dGTP and dTTP; a chelating agent; a salt; a buffer; a stabilizing agent and nuclease-free water.

Other embodiments and advantages of the invention are set forth in part in the description, which follows, and in part, may be obvious from this description, or may be learned from the practice of the invention.

DESCRIPTION OF THE FIGURES

FIG. 1 Illustrates the pncA gene sequence plus 100 flanking base pairs as well as the reverse compliment sequence, the protein sequence, and the primers sequences.

FIG. 2 Illustrates the nucleotide sequence of H37RV Gene strain as well as the sequences of the TB 16S ribosomal RNA gene sequencing primers.

FIG. 3 Illustrates the rpoB gene conferring sensitivities/resistance to Rifampin as well as the forward and reverse primer sequences for rpoB.

FIG. 4 Illustrates the *Mycobacterium tuberculosis* H37Ra, complete genome (Gen Bank: CP0006111.1) GyrA Gene and three sets of forward and reverse primers.

FIG. 5 *Mycobacterium tuberculosis* H37Ra, complete genome (Gen Bank: CP000611.1) catalase-peroxidase-peroxynitritase T katG and three sets of forward and reverse primers.

FIG. 6 Illustrates the cycle threshold of Gyrase A and IS 6110 assays.

FIG. 7 Illustrates Gyrase A assay and the IS 6110 assay using sequence isolates by cycle number vs. Ct value.

FIG. 8 Illustrates Gyrase A assay and the IS 6110 assay using sequence isolates vs cycle threshold (et).

FIG. 9 Summary of results achieved in sequencing the influenza A genome using various primer pair collections with ion torrent sequencing methodology.

FIG. 10 Characterization of primer pairs for whole-genome ion torrent sequencing of influenza A (H3N2).

FIG. 11 (A) Gene sequence of pncA showing coding regions as shaded, and (B) pncA forward and reverse primers utilized in PCR tiling and pncA regions P1-P4.

DESCRIPTION OF THE INVENTION

Rapid analysis of genes associated with drug resistant strains is a major challenge for successful treatment of many diseases and disorders. Real-time geographical surveillance of emerging MTB drug resistance would facilitate more appropriate treatment strategies (e.g., drug, antibiotic, chemical). Currently, available molecular methods such as the GenoType® MTBDRplus LPA offer limited detection capabilities, particularly when novel/uncommon amino acid substitutions are within known drug resistance regions or when undiscovered amino acid mutations impact drug resistance. Also, current methodology including Ion Torrent protocol requires multi-steps, ancillary equipment and increased expense, and is labor intensive.

A simplified semiconductor sequencing protocol for rapid characterization of full-length genes and genome has been surprisingly discovered. The invention comprises a standardized protocol utilizing semiconductor sequencing and preferably Ion Torrent sequencing of full-length genes. The protocol enables sequencing of entire coding regions implemented allowing characterization of known mutations and discovery of new polymorphisms. This protocol also enables the sequencing of mega-bases of nucleotide information such that complete genomes of cells and organisms can be determined and the genetic polymorphism readily mapped and identified. Preferably the cells or organisms are disease causing prokaryotic or eukaryotic cells, or yeast or fungal cells. Preferred disease causing organisms include strains of bacteria, virus, fungus, and parasites. Exemplary organisms include, but are not limited to Mycobacteria (e.g., *M. tuberculosis*), influenza virus (e.g., H5N1, H1N1, H1N1, H7N9), Respiratory Syncytial Virus, HIV, and *Plasmodium* (e.g., *Plasmodium falciparum*).

This relatively rapid (e.g. 1, 2, or 3 days, or less), standardized, cost-effective protocol allows for full length analysis of genes such as, for example, rpoB, katG, gyrA, pncA and rrs MTB genes associated with first and second-line MTB drug resistance (see FIGS. 1-5). The protocol was evaluated using 26 geographically diverse clinical isolates collected in South Africa including MDR and XDR strains with next-generation Ion Torrent Personal Genome Machine (PGM). The sequencing data obtained from this developed methodology were compared to the HAIN LPA and genotyping DST data from culture. This methodology for the first time enables sequencing entire coding regions for genes implemented in resistance allowing characterization of known mutations and discovery of new polymorphisms. Previously uncharacterized substitution mutations were identified on the rrs, rpoB, katG, pncA and gyrA genes.

The present invention offers significant potential for next-generation instruments to be more utilized in resource deprived environments such as Africa, Asia, and India. Specifically, the current invention improves and streamlines the up-front library preparation process. Methodology of the invention does not require the use of expensive ancillary equipment pieces typically utilized or required by the manufacturer. Specifically, the standardized procedure of the invention does not require an Agilient Bioanalyzer for DNA quantifications; the OneTouch ePCR system for emulsification PCR step, or the PipinPrep for gel excision. Additionally, since the protocol of the invention involves re-sequencing full-coding genes (not necessarily full genomes) the Bioruptor is not required for shearing DNA into smaller pieces. Additionally, it is not necessary to sequence the entire genome and then identify genes. The method and tools of the invention allow for pre-selection of the genes and/or regions of interest that are to be sequenced. As the Agilent 2100 BioAnalyzer, OneTouch, PipinPrep, and Bioruptor all require additional training for use, consume valuable laboratory bench space, and are extremely expensive, the invention represents a significant advance and improvement over convention methodologies.

The sequencing protocol of the invention is exemplified herein using Ion Torrent sequencing as this sequencing method has been applied to *M. tuberculosis*. As believed to clear to those skilled in the art, the protocol involves semiconductor sequencing, with is exemplified by on Torrent sequencing, and, as such, involves the sequencing of large numbers of different regions simultaneously. The sequencing and nucleic acid methodologies are applicable to any series of genes, genomes or nucleic acid sequences.

The invention also includes a methodology for selecting primer pairs for sequencing a target of interest. Primer pairs are preferably selected with matched annealing and melting temperature as to the target. Preferably, melting and annealing temperatures are based on sequence characteristics such as the GC content of the sequence, the possibility of self-hybridization of the primer (e.g., forming hairpin loops within the primer), and possible structures near the binding site. Preferably the primers do not self-hybridize under the conditions of sequencing. Preferably the GC content of primers is between about 25% and 50%, more preferably between about 30% and 40%, more preferably between about 25% and 35%, and also more preferably between about 40% and 50%. Thus, primer sequences of the target are selected for hybridization based on sequence characteristics such that all of the primer pairs utilized for the target will have similar melting and/or annealing temperatures to the target. Preferably primer sequences contain no regions of reasonably possible self hybridization of the primer sequence. Preferably primer pairs are matched for annealing, and/or disassociation temperatures which may be within 5° C., within 4° C., with 3° C., within 2° C., with 1° C. and more preferably the same annealing temperature, the same melting temperature or both. Primer pairs preferably generate amplicons of between about 500 to about 2,000 nucleotides (NT) in length that represent overlapping segment of the target, more preferably between about 600 and 1,500 NT, more preferably between about 700 and 1.300 NT, more preferably between about 800 and 1,200 NT, more preferably between about 900 and 1,100 NT, and more preferably about 1,000 NT. Primers are generally between 12 NT and 45 NT in length, more preferably between 15 and 35 NT, and more preferably between about 18 and 25 NT. Although not a rule, generally longer primers have a lower GC content. Exemplary primers pairs are identified for the pncA gene (see FIG. 1), the H37RV gene strain (see FIG. 2), the rpoB, gene (see FIG. 3), the GyrA gene (see FIG. 4, and the katG gene (see FIG. 5).

Figure 6:
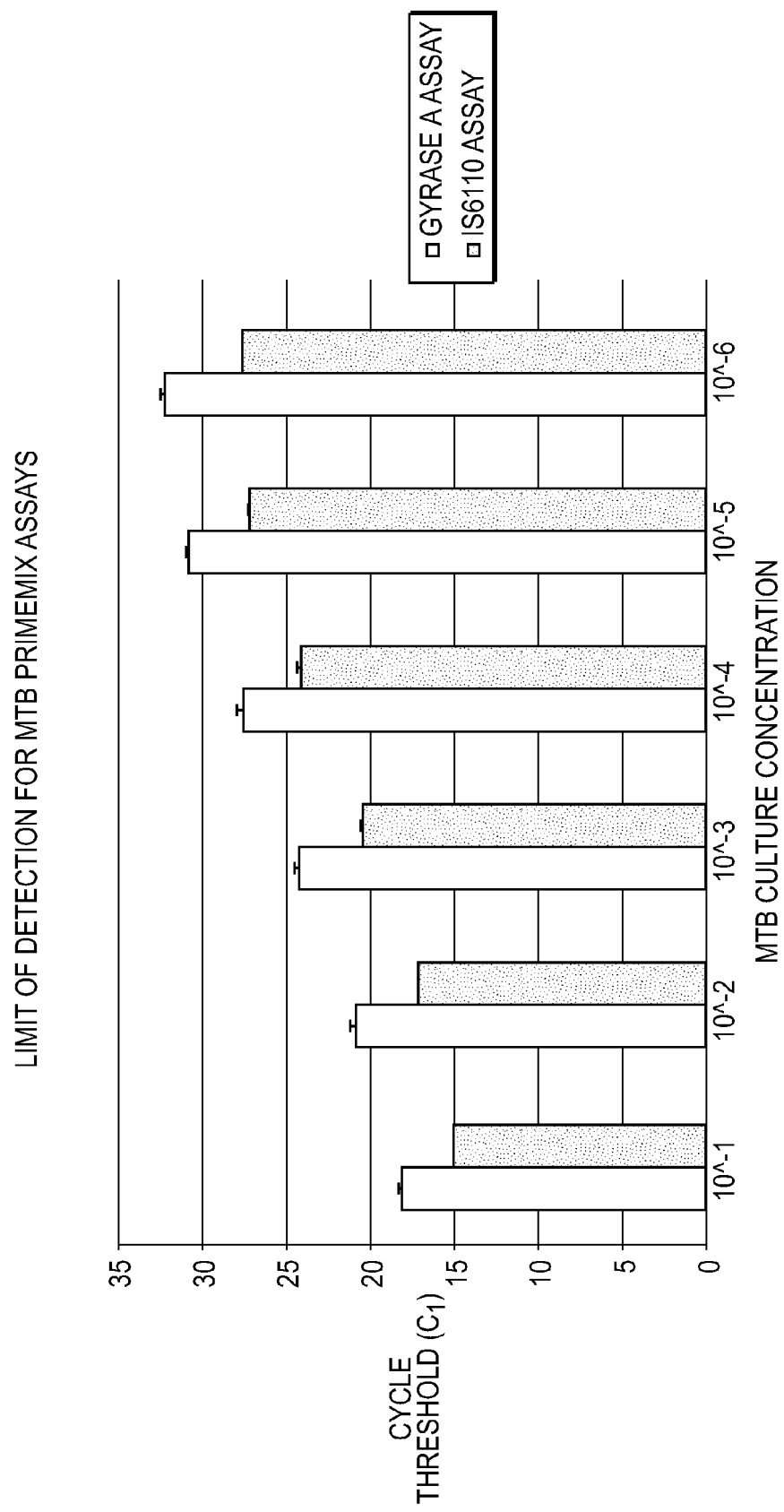

In one embodiment of the invention, a semiconductor sequencing protocol was determined for five genes of *M. tuberculosis* for determining drug resistance in MDR and XDR strains (e.g. cumulatively sequencing 11.4 kb per isolate). The *M. tuberculosis* rpoB gene encodes a 1,178 amino acid beta subunit for an RNA dependent DNA polymerase enzyme. Mutations within an 81-bp "core region" of the rpoB gene are responsible for approximately 95% of rifampin resistance in *M. tuberculosis* strains. Three of these mutations at positions 516 (D→V), 526 (H→Y/D), and 531 (S→L) constitute the majority of mutations within this region. Of the 21 rifampin-resistant strains characterized in this study, 11 (52.4%) carried the S531L mutation, 7 (33.3%) contained an amino acid substitution at position 516, and 3 (14.3%) contained a mutation at position 526 of the rpoB gene (Table 1). The most prevalent rpoB substitution observed at position 516 is a valine (D516V). Ion Torrent sequencing according to the invention revealed that 6 of 7 strains contained a rarer glycine residue (D516G) at this position (Table 1). These 6 strains were shown as absent for both mutant and wild type bands by LPA (Table 1). Similarly an uncommon amino acid substitution was identified at position 526 in the rpoB gene. The most prevalent amino acid substitution reported at position 526 in the rpoB gene is a histidine to tyrosine or aspartic acid (H526 Y/D). Ion Torrent sequencing revealed 1 of 3 isolates contained an uncommon arginine (R) residue (H526R) that by HAIN LPA was shown to be absent for both wild type and mutant bands (Table 1). While absence of wild type and mutant bands in a sample are interpreted as resistant according to LPA testing, there remains ambiguity since the type of amino acid change is not directly characterized. This underscores the utility of Ion Torrent sequencing for resistance surveillance, and discovery of novel amino acids in circulating MTB strains.

TABLE 1

Summary of 10 amino acid mutations in the first 900 amino acid residues* of the rpoB gene of 26 (14 MDR, 7 XDR and 5 fully susceptible) *M. tuberculosis* isolates from South Africa deduced by Ion Torrent sequencing, Hain LPA genotyping and culture.

| Isolate No. | Amino Acid Substitution(s)** of rpoB gene (3619 bps) | Rifampin Result by Ion Torrent* | HAIN LPA | Bacter MGIT 960 |
|---|---|---|---|---|
| 9 | S531L | Resistant | Resistant | Resistant |
| 1 | S531L, V194I | Resistant | Resistant | Resistant |
| 1 | S531L, Y645H | Resistant | Resistant | Resistant |
| 1 | H526D | Resistant | Resistant | Resistant |
| 1 | H526Y, S509R | Resistant | Resistant | Resistant |
| 1 | H526R | Resistant | Resistant | Resistant |
| 5 | wild type** | Sensitive | Sensitive | Sensitive |
| 6 | D516G, L533P | Resistant | Resistant | Resistant |
| 1 | D516V | Resistant | Resistant | Resistant |

*There were 5 rpoB amino acid substitutions (R908C, Q1042H, P1043A, I1187T, and V1249F) noted in at least 1 strain at the 3' end (residues 900-1253).
**Compared to the sequenced H37Rv reference strain.

The katG gene encodes catalase peroxidase, an enzyme that converts isoniazid (INH) into the active form. The majority of isoniazid resistance is associated with katG codon 315 (S315T), although mutations in the promoter region of inhA and nod also contribute to resistance. Of 26 strains assessed, 16 (62%) contained the characteristic serine-to-threonine amino acid substitution at position 315 (S315T) conferring isoniazid resistance (Table 2). These sequencing results exhibited 100% concordance with comparisons made using the HAIN LPA and culture DST.

TABLE 2

Summary of 4 amino acid mutations in the katG gene of 26 (14 MDR, 7 XDR and 5 fully susceptible) *M. tuberculosis* isolates from South Africa deduced by Ion Torrent sequencing, Hain LPA genotyping and culture

| Isolate No. | Amino Acid Substitution(s)** of katG gene (2447 bps) | Rifampin Result by Ion Torrent* | HAIN LPA | Batter MGIT 960 |
|---|---|---|---|---|
| 11 | S315T | Resistant | Resistant | Resistant |
| 5 | S315T, R463L | Resistant | Resistant | Resistant |
| 1 | W191R, R463L | Sensitive | Sensitive | Sensitive |
| 7 | wild type** | Sensitive | Sensitive | Sensitive |
| 1 | R463L | Sensitive | Sensitive | Sensitive |
| 1 | N138H | Sensitive | Sensitive | Sensitive |

*Rifampin resistance is known to occur in rpoB at positions 531 (S→T), 526 (H→Y/D), and 516 (D→V).
**Compared to the sequenced H37Rv reference strain.

Pyrazinamide (PEA) is a synthetic derivative of nicotinamide that has been used as a first-line drug to fight tuberculosis since 1952. Standard DST for PZA is complicated due to an acidic pH requirement in vitro, which inhibits *M. tuberculosis* growth and complicates accurate phenotypic assessment. PEA resistance is attributed to mutations in the pncA gene which encodes a pyrazinamidase. These resistance conferring mutations are numerous and include amino acid substitutions, frameshifts and stop codon mutations. Seven mutations were characterized from the 26 South African isolates assessed, including one silent mutation, 5 amino acid substitutions, and one chain termination mutation. The Q122 (Stop) termination mutation (Table 3) observed in one isolate is novel, having not been reported elsewhere. The difficulty in PZA phenotypic assessment and the variability of mutations along the pncA gene further underscores the added value of Ion Torrent gene sequencing to assess mutations in this hyper variable MTB gene.

TABLE 3

Summary of 6 amino acid mutations in the pncA gene of 26 (14 MDR, 7 XDR and 5 fully susceptible) *M. tuberculosis* from South Africa deduced by Ion Torrent sequencing and culture

| Isolate No. | Amino Acid Substitution(s)** in the pncA gene (3619 bps) | Pyrazinamide Result by Ion Torrent* | Bacter MGIT 960 |
|---|---|---|---|
| 3 | C14R | Resistant | Resistant |
| 1 | A102V | Resistant | Resistant |
| 1 | Q122 (stop) | Resistant | Resistant |
| 16 | wild type** | Sensitive | Sensitive |
| 1 | V139G | Resistant | Resistant |
| 1 | R154G | Resistant | Resistant |
| 2 | L172P | Resistant | Resistant |
| 1 | Silent (C195T) | Sensitive | Sensitive |

*pyrazinamide resistance is known to occur in 25 mutations described by Mphahele et al (23).
**Compared to the sequenced H37Rv reference strain. One strain contained a silent (synonymous) nucleotide mutation at position 195 (C→T).

The primary target of fluoroquinolones (FQ) in *M. tuberculosis* is DNA gyrase, a type II topoisomerase composed of two A and B subunits encoded by the gyrA and gyrB genes, respectively. Amino acid substitutions located within a short region of the gyrA gene known as the quinolone resistance-determining region (QRDR), account for the majority of known FQ resistant tuberculosis strains. Substitution mutations in the QRDR at positions 88, 90, and 94 were observed in 10 of 26 (38.5%) sequences from this study (Table 4). Three of these 10 strains contained substitutions at position 94 in the gyrA gene; two were noted as D940 substitutions, and one was a D94Y substitution. Both D940 and D94Y have been characterized as substitutions and both amino acid substitutions at codon 94 give rise to similar levels of FQ antibiotic resistance. Of the strains assessed, the gyrA gene was the most variable containing nine amino acid substitutions in the 26 clinical isolates assessed. Furthermore, two of these gyrA codons (549 and 613), exhibited heterogeneous residues (Table 4), an advantage of performing Ion Torrent sequencing over HAIN LPA and DST.

TABLE 4

Summary of 10 amino acid mutations in the gyrA gene of 26 (14 MDR, 7 XDR and 5 fully susceptible) *M. tuberculosis* isolates from South Africa deduced by Ion Torrent sequencing and culture

| Isolate No. | Amino Acid Substitution(s)** in the gyrA gene (2664 bps) | Rifampin Result by Ion Torrent* | Bacter MGIT 960 |
|---|---|---|---|
| 3 | E21Q, S95T, G2475S, G668D | Sensitive | Sensitive |
| 2 | E21Q, D94G, S95T G668D | Resistant | Resistant |
| 1 | E21Q, G88C, S95T, G668D | Resistant | Resistant |
| 10 | E21Q, S95T, G668D | Sensitive | Sensitive |
| 1 | wild type** | Sensitive | Sensitive |
| 1 | E21Q, S95T, G668D, Q613Q/E+ | Sensitive | Sensitive |
| 1 | E21Q, S95T, G668D, L5495/L+ | Sensitive | Sensitive |
| 1 | E21Q, D94Y, S95T, G668D | Resistant | Resistant |
| 6 | E21Q, A90V, S95T, G247S, G668D | Resistant | Resistant |

*Fluroquinolone resistance is known to occur in gyrA at position 88 (G→C), 90 (A→V), 91 (S91P) and 94 (D→H).
**Compared to the sequenced H37Rv reference strain.
+There is a heterozygous nucleotide mutation in a proportion of Ion Torrent reads; the mutation confers a mixed amino acid substitution.

Emerging cases of XDR tuberculosis defined as MDR cases having acquired additional resistance to FQ, i.e., ofloxacin, and at least one of the three injectable 'second-line drugs', i.e., amikacin (AMK), kanamycin (KAN), or capreomycin (CAP), have become a public health threat in developing countries worldwide. The majority of resistance to second line drugs is associated with mutations in codons 1401 (A1401G), 1402 (C1402T), and 1484 (G1483T) in the 16 S ribosomal RNA rrs gene. Analysis of African MTB strains revealed that 7 of 26 (27%) were defined as XDR as evident by nucleotide mutation at position 1401 (A14010) (Table 4). Three additional nucleotide mutations at positions 492, 514, and 878 were also discovered (Table 5) in strains from this analysis. The G878A is a novel nucleotide mutation but was shown to be sensitive to AMK, KAN, and CAP according to DST.

TABLE 5

Summary of 4 nucleotide mutations in the rrs (16s) gene of 26 (14 MDR, 7 XDR and 5 fully susceptible) *M. tuberculosis* isolates from South Africa deduced by Ion Torrent sequencing and culture.

| Isolate No. | Amino Acid Substitution(s)** in the rrs (16s) gene (1680 bps) | Kanamycin Result by Ion Torrent* | Bacter MGIT 960 |
|---|---|---|---|
| 1 | G878A | Sensitive | Sensitive |
| 12 | wild type** | Sensitive | Sensitive |
| 1 | A514C, A1401G | Resistant | Resistant |
| 6 | A1401G | Resistant | Resistant |
| 3 | A514C | Sensitive | Sensitive |
| 1 | C492T | Sensitive | Sensitive |
| 1 | C492T, A514C | Sensitive | Sensitive |
| 1 | A514C | Sensitive | Sensitive |

*Aminoglycoside resistance is known to occur at positions 1401 (A→G), 1402 (C→T), and 1484 (G→T).
**Compared to the sequenced H37Rv reference strain.

Previous studies have shown that mutations in katG codon 463, and gyrA codon 95 are genetic markers for categorizing strains into epidemiological genetic Groups 1, 2, and 3, and that these codons have no effect on antibiotic resistance. Group 1 strains are genetic ancestors of Group 2 and Group 3 strains that link the predominately non-human *mycobacterium* genus (*M. microti* and *M. bovis* strains) with human *M. africanum* and *M. tuberculosis* lineages. As evident by substitution mutations in katG codon 463 and gyrA codon 95, a total of 7 of 26 (27%), 18 of 26 (69%), and 1 of 26 (4%) of the African isolates characterized in this study were members of genetic Group 1, 2, and 3, respectively. Tracking Group 1 organisms is important in terms of MTB detection since several isolates belonging to genetic Group 1 lack Insertion Sequence 1661 (IS-1661), a common genetic target for several PCR-based MTB detection assays.

The Ion Torrent protocol for MTB drug resistance can be easily integrated into low resource settings throughout countries and regions such as Africa, India, and China. The Ion Torrent methodology does not require the use of expensive ancillary equipment such as Agilent 2100 BioAnalyzer, DiaGenode Bioruptor® Sonication System, Ion OneTouch System™, ultracentrifuges, or the Pippin Prep™ Workstation as current Ion Torrent protocols recommend. This is significant since these instruments and needed accessories and consumables can be expensive, require large laboratory footprints, and often require routine maintenance.

In contrast to the GenoType® MTBDRplus or MTBDRsl Line Probe Assay (LPA), the Ion Torrent PGM protocol provides full-length characterization of genes, making possible discovery of new amino acid substitutions that could potentially be missed by LPA since LPA is limited to only known mutations. Using the protocol, several uncommon amino acid changes in clinical field isolates have been found. Furthermore, the extensive depth of sequence coverage from the Ion Torrent allows for discovery of heterogeneous or mixed strain genetic populations within an isolate.

The scalability of Ion Torrent sequencing permits expansion to include megabases of additional genes on a single chip. The methodology of the invention is expandable beyond the five full-length MTB genes to include all 16 plus genes that currently constitute MTB drug resistance. Full-length gene analysis using the Ion Torrent PGM will identify novel mutations that, when correlated to phenotypic minimal inhibitory concentration (MIC) testing, identify new tuberculosis resistant residues as well as the cumulative inhibitory effect of multiple mutations.

Another embodiment of the invention is directed to megabase sequence identification utilizing semiconductor sequencing protocols. Megabase sequencing according to the invention involves selection of primer pairs that amplify different sections of the target sequence whereby the collection of sections represent the entirety of the target sequence. Preferably the sections overlap to a degree that permits alignment of the resulting amplicons forming the complete target sequence. Primer pairs are preferably designed to form amplicons with lengths of about 0.5 k to about 5 k nucleotides, preferably about 0.6 k to about 3 k nucleotides, more preferably about 0.7 k to about 2 k nucleotides, and more preferably about 0.8 k to about 1 k nucleotides. Primer pairs are preferably of similar GC contact such that the annealing or hybridization temperatures are as similar or preferably within about 5° C., more preferably within about 2° C., and more preferably within about 1° C. Also preferred is that the hybridization disassociation temperatures be similar, such that annealing and disassociation occur at very similar temperature for polymerization and PCR. In annealing and disassociation, the length of the primer influences the temperature profile, thus similar length for the all or at least most of the primers is preferred. Primer lengths are preferably about 15-30 nucleotides, more preferably about 20-28 nucleotides, and more preferably about 18 to 25 nucleotides. Although it is preferred that all of the primers have such similar characteristics, megabase sequencing can be performed when greater than about 80% of the primers share one or more characteristics, more preferably 85% or more, more preferably 90% or more, and even more preferably 95% or more. In accordance with the utilization of such similar primers, a PCR reaction is performed with one target nucleic acid to be amplified with a mixture of all primer pairs. Also preferred is performance of duplicate PCR analysis on identical mixtures. The number of cycles can range from 10 to 50 or more and, preferably temperature cycling is performed in accordance with convention PCR temperature and reaction conditions.

The following examples illustrate embodiments of the invention, but should not be viewed as limiting the scope of the invention.

EXAMPLES

Clinical Isolates

A total of 26 geographically diverse clinical isolates, representing drug-sensitive, MD, and XDR tuberculosis strains were obtained from sample archives of the University of Pretoria, South Africa, and the National Institute for Communicable Diseases (NICD), Sandringham, South Africa. The H37Rv MTB lab strain was included as a sequencing control throughout the protocol. All MTB isolates used were archived strains from pure culture MGIT™ 960 System tubes (Becton Dickinson, Sparks, Md.) with species identification and genotypic resistance to rifampin and isoniazid determined using the Genotype® MTBDplus assay (HAIN LifeSciences, Germany) according to manufacturer's instructions. Phenotypic resistance for first and second line drugs was performed using the MGIT™ 960 System as previously described. Critical concentrations for ofloxacin and kanamycin (second line drugs) were 2.0 µg/mL and 5.0 µg/mL, respectively. Resistance to first and second line drugs was determined using standard diagnostics algorithms.

DNA Preparation.

MTB isolates were handled in blinded fashion throughout. MTB samples (0.5 mL) were pipetted into cryovial tubes containing 1.5 mL PrimeStore Molecular Transport Medium® (a molecular transport medium) (Longhorn Vaccines & Diagnostics, San Antonio, Tex.). Inactivated samples were transported from South Africa to San Antonio, Tex., USA at ambient temperature (3-4 days) and stored at 5° C. until used. Total DNA (50 µl) was purified from a 200 µl aliquot of PrimeStore MTM® containing inactivated culture using a Qiagen® EZ1® Advanced Robot and EZ1 DNA Tissue Kit (Cat No. 953034) according to manufacturer's recommendations (Qiagen Inc., Germantown, Md.).

Primer Design

Novel PCR primers were designed for amplification of full-length coding regions for each MTB gene of interest (Table 6).

TABLE 6

PCR amplification primers used for full length analysis of MTB Genes.

| Amplification Target | Forward | Reverse | Amplicon (bp) |
|---|---|---|---|
| rpoB | 5'-TCCTCTAAGGGCTCTCGTT-3' 19 nt (SEQ ID NO 1) | 5'-GTCAGGTACACGATCTCGT-3' 19 nt (SEQ ID NO 2) | 1625 |
| rpoB11 (2 half) | 5'-ATCGAAACGCCGTACCGCAA-3' 20 nt (SEQ ID NO 3) | 5'-TGACGTCGAGCACGTAACTCCCT-3' 23 nt (SEQ ID NO 4) | 2056 |
| katG | 5'-ACACCAACTCCTGGGAAGGAAT-3' 22 nt (SEQ ID NO 5) | 5'-TGATCGCACATCCAGCACATTT-3' 22 nt (SEQ ID NO 6) | 2447 |
| pncA | 5'-GACGGATTTGTCGCTCACTAC-3' 21 nt (SEQ ID NO 7) | 5'-GCCGGAGACGATATCCAGAT-3' 20 nt (SEQ ID NO 8) | 960 |
| gyrA | 5'-AAGGATGTTCGGTTCCTGGAT-3' 21 nt (SEQ ID NO 9) | 5'-TAACACTCGTACCCGGCT-3' 18 nt (SEQ ID NO 10) | 2665 |
| rrs (16s) | 5'-TTCTAAATACCTTTGGCTCCCT-3' 22 nt (SEQ ID NO 11) | 5'-TGGCCAACTTTGTTGTCATGCA-3' 22 nt (SEQ ID NO 12) | 1680 |

(5 genes) 11,432 BP total

Primer pairs for rpoB (2 sets of primers), katG, pncA, gyrA, and rrs (16s) gene amplification were designed using the genome sequence of M. tuberculosis H37Rv strain as reference (GenBank accession no, NC_000962). Primer secondary structure, melting temperature, and potential primer-dimer formation were determined using LaserGene 9.1 (DNAStar, Madison, Wis.) and PrimerExpress 3.0 (Life Technologies, Foster City, Calif.). All oligonucleotides were synthesized using standard, de-salted primers (Integrated DNA Technologies (IDT), San Diego, Calif.).

PCR Amplification.

Amplification reactions for all MTB gene targets were designed and optimized to be used under one standardized set of thermocycling parameters. All PCR 'mastermixes' were prepared using Platinum Taq DNA Polymerase, 10× Buffer, and 50 mM $MgCl_2$ (P/N 10966-034; Life Technologies, Foster City, Calif.). Amplification was carried out in a 50 μl final volume reaction mixture containing 24.1 μl Ambion Nuclease-Free Water (Cat No. AM 9932; Life Technologies, Foster City, Calif.), 5 μl 10×PCR Buffer, 2 μl 50 mM $MgCl_2$ (2 mM final), 0.4 μl PCR Nucleotide Mix Ultrapure dNTPS (200 μM final for each dNTP; P/N 77119; USB, Santa Clara, Calif.), 0.5 μl Platinum Taq DNA Polymerase (2.5 Units final), and 2 μl primer blend (rpoB, katG, pncA, gyrA, or rrs genes; 0.4 μM final for each primer). To each 34 μl 'mastermix' reaction mixture, 16 μl extracted DNA was added to bring the total volume to 50 μl. Reactions were carried out in MicroAmp Optical 96-Well Reaction Plates (P/N N801-0560, Life Technologies, Foster City, Calif.) and capped using MicroAmp 8-Cap Strips (P/N 4323032. Life Technologies. Foster City, Calif.), Amplification was performed using an ABI 2720 thermocycler (Life Technologies, Foster City, Calif.). Thermocycling parameters were 95° C. for 2 minutes, followed by 40 cycles at 95° C. for 30 seconds, 55° C. for 15 seconds, and 72° C. for 2 minutes with final extension at 72° C. for 5 minutes. Resulting amplicons were confirmed by addition of 5 μl PCR product with 1 μl GelPilot Loading Dye 5× (P/N 1037649; Qiagen, Germantown, Md.) on 1% (wt/vol) Molecular Biology Grade Agarose (Cat No. BP1356; Fischer Scientific, Pittsburg, Pa.) with ethidium bromide (0.1 μg/mL final; Cat No 161-0433; Bio-Rad, Hercules, Calif.). Electrophoretic separation of products was carried out for 60 minutes at 0.4 mV $cm^2$ in 1×Tris Borate-EDTA (TBE) Buffer (Cat No. 1B70153; IBI Scientific, Peosta, Iowa). Amplicons were visualized under UV transillumination, and size estimation made using a TrackIt 1 kb Plus DNA Ladder (P/N 10488-085; Life Technologies, Foster City, Calif.). After visualization, the remaining PCR reaction for each clinical isolate gene amplification (~45 μL) corresponding to rpoB, katG, pncA, gyrA, and rrs (16s) targets were transferred to a single microcentrifuge tube. Pooled genes corresponding to each clinical isolate were subjected to PCR purification and eluted in 50 μl Low Tris-EDTA (TE) (Cat No. 602-1155-010; Life Technologies, Foster City, Calif.) using the MinElute Reaction Cleanup Kit (Cat No. 28204; Qiagen, Germantown, Md.) according to manufacturer's instructions. The concentration and purity of DNA was determined spectrophotometrically using a NanoDrop ND 1000 (Thermo Fischer Scientific, Wilmington, Del.).

Ion Torrent Library Preparation.

Barcoded libraries were generated using the Ion Xpress Plus Fragment Library Kit (Cat No. 4471269, Life Technologies, Foster City, Calif.) and the Ion Xpress DNA Barcoding 1-16 Kit (Cat No. 4468654, Life Technologies, Foster City, Calif.) according to a modified version of the protocol outlined in the ion Xpress Plus gDNA and Amplicon Library Preparation.

Amplicon Shearing.

Chemical shearing was performed using 1-3 μg DNA containing an approximate equimolar pool of rpoB, katG, pncA, gyrA, and rrs (16s) gene amplicons. DNA shearing was performed in a 50 μl total reaction volume by combining 5 μl ion Shear Plus 10× Reaction Buffer, 10 μl enzyme, and 35 μl pooled DNA template (Ion Xpress Plus Fragment Library Kit, Cat No. 4471269, Life Technologies, Foster City, Calif.). The reaction mixture was incubated at 37° C. for 45 minutes, terminated using 5 μl Ion Shear Stop Buffer, and stored on ice until purification. Sheared DNA was purified using Agencourt Ampure XP-PCR Purification beads (P/N A63880; Beckman Coulter, Brea, Calif.) with Dynal magnetic bead stand (Cat No. 123-21 ft Life Technologies, Foster City, Calif.) according to manufacturer's recommendations. Briefly, 99 μl Agencourt beads was mixed with 50 μl ion shear reaction, incubated for 5 minutes at room temperature, placed on a magnetic stand, washed twice with 70% (v/v) ethanol, and eluted using 12 μl Low TE Buffer (Cat No. 602-1155-010; Life Technologies Inc., Foster City, Calif.).

Adaptor Ligation.

Adaptor ligation was performed in a 0.2 mL low bind PCR tube (PIN PCR-02-L-C; Axygen Inc., Union City, Calif.) by combining 12 μl sheared amplicon with 1.25 μl Ligase Buffer, 1.25 μl P1-1A Adaptor Mix (ion DNA Barcoding 1-16 Kit, Cat No. 4468654 Life Technologies. Foster City, Calif.) and 0.2 μl DNA Ligase (Ion Xpress Plus Fragment Library Kit, Cat No. 4471269, Life Technologies, Foster City, Calif.). The mixture was pipetted up and down 5 times and incubated at room temperature (22-25° C.) for 30 minutes, Adaptor ligation reactions were purified and eluted in 10 μl Low TE Buffer using the Agencourt Ampure XP-PCR Purification beads (P/N A63880; Beckman Coulter, Brea, Calif.) with the Dynal magnetic bead stand (Cat No. 123-21D; Life Technologies, Foster City, Calif.) according to manufacturer's recommendations.

Nick Translation and Barcode Amplification.

Amplicon pools from each patient sample were barcoded using the Ion DNA Barcoding 1-16 Kit and Ion Xpress Fragment Library Kit (Part Nos. 4468654 and 4471269, respectively; Life Technologies, Foster City, Calif.). To maximize yields reactions were scaled 2× by combining 40 μl Platinum PCR SuperMix High Fidelity, 4.4 μl of Ion Primer Mix (BC X where X=barcode 1-16) and 10 μl of ligated DNA. Amplification vas performed using an ABI 2720 thermocycler (Life Technologies, Foster City, Calif.). Thermocycling parameters comprised 72° C. for 20 minutes, 95° C. for 5 minutes, followed by 10 cycles of 95° C. for 15 seconds. 58° C. for 15 seconds and 68° C. for 1 minute. Following amplification, bar-coded samples were purified and eluted in 50 μl of Low TE (Cat No 602-1155-010; Life Technologies, Foster City, Calif.) using the MinElute Reaction Cleanup Kit (Cat No. 28204; Qiagen, Germantown Md.) according to manufacturer's instructions. DNA concentration and purity was determined by spectrophotometric analysis using a NanoDrop ND 1000 (Thermo Fischer Scientific, Wilmington, Del.). Ranges for purified bar-coded samples are typically 150-300 ng/μl with A260/280 purity of 1.7-1.9. Equimolar concentrations (~2-3 μg of each bar-coded sample) were combined into a single 1.5 mL nuclease-free microcentrifuge tube and used for size selection.

Size Selection.

The appropriate volume of GelPilot 5× Loading Dye (P/N 1037649; Qiagen, Germantown, Md.) was added to the pooled bar-coded MTB library tube and loaded onto a 1% (w/v) agarose gel (Cat No BPI 356 Fischer Scientific, Pittsburg, Pa.) containing ethidium bromide (0.1 μg/mL final; Cat No 161-0433; Bio-Rad. Hercules, Calif.). The bar-coded library was electrophoresed for 60 minutes at 0.4 in V cm² in 1×TBE Buffer (Cat No. 1B70153; 1131 Scientific, Peosta, Iowa) and visualized under UV transillumination, Size estimations were determined using a TrackIt 1 kb Plus DNA Ladder (P/N 10488-085; Life Technologies, Foster City, Calif.). Gel excision was performed under UV transillumination using a sterile scalpel blade excising out a target region between 75-200 bp. Excised agarose gel slices were placed into sterile 1.5 mL microcentrifuge tubes and subjected to DNA purification using the PureLink Quick Gel Extraction Kit (Cat No. K210012; Life Technologies, Foster City, Calif.) according to manufacturer's instructions. Concentration and purity values for the barcoded DNA library were determined spectrophotometrically using a NanoDrop ND 1000 (Thermo Fischer Scientific, Wilmington, Del.). The recommended library input for emulsion PCR is ~140-560×10⁶ molecules per 18 μl. This range was achieved by a 1:1000 dilution using library stock and nuclease-free water.

Emulsion Polymerase chain Reaction (emPCR).

Emulsion Polymerase chain reaction was performed in a 1 mL reaction volume using the Ion Template Preparation Kit (Cat No. 4469000; Life Technologies, Foster City, Calif.) by adding 582 μl nuclease-free water, 200 μl 5×PCR. Reagent Mix, 100 μl 10×PCR Enzyme Mix, 100 μl Ion Sphere Particles, and 18 μl diluted library template. The preparation was mixed thoroughly followed by brief centrifugation in a microcentrifuge. Emulsion was achieved using the Ultra-Turrax Tube Drive (Life Technologies, Foster City, Calif.). A total of 9 mL chilled Emulsion Oil (Ion Torrent Preparation Kit; Cat No. 4469000, Life Technologies, Foster City, Calif.) was added to an Ion Template Preparation Tube (Cat No. 4467226, Life Technologies, Foster City, Calif.). The emulsion tube was placed and locked onto the IKA Ultra-Turrax Tube Drive and initiated. While the tube was in motion, the entire 1 mL PCR master mix solution was dispensed into the cap port and mixed for 5 minutes. The mixed emulsion was transferred to a 96-well PCR plate and amplified using an ABI 2720 thermocycler (Life Technologies, Foster City, Calif.) using the following thermocycling parameters; 94° C. for 6 minutes, followed by 40 cycles at 94° C. for 30 seconds, 58° C. for 30 seconds, and 72° C. for 90 seconds; followed by 5 cycles at 94° C. for 30 seconds, and 68° C. for 6 minutes.

Ion Sphere Particle (ISP) Recovery and Qubit Measurement.

Ion Sphere Particles were recovered using reagents supplied in the Ion Xpress Template Kit (Cat No. 4469001, Life Technologies, Foster City, Calif.) according to manufacturer's protocol (Ion Xpress Template Kit User Guide v2.0, pages 18-19). Quantification of recovered particles was performed using a Qubit 2.0 Fluorometer (Life Technologies, Foster City, Calif.) and an Ion Sphere Quality Control Kit (Cat No. 4468656, Life Technologies, Foster City, Calif.) according to manufacturer's recommendations (Ion Xpress Template Kit User Guide, page 25-26). The optimal amount of template-positive ion sphere particles (ISPs) is between 4-50%. Relative fluorescent unit (RFU) values obtained outside of this range were not pursued into subsequent ISP enrichment.

ISP Enrichment.

ISPs were enriched using reagents supplied in the Ion Xpress Template Kit, Ion Sequencing Kit, and DynaBeads MyOne Streptavidin C1 beads (Cat Nos. 4469001, 4468997 and 650.01 respectively; Life Technologies, Foster City, Calif.) according to the manufacturer's protocols (Ion Xpress Template Kit User Guide v2.0, pages 15-17).

Ion Torrent 314 Chip Preparation and PGM Sequencing.

Ion Torrent 314 Chips (Cat No. 4462923; Life Technologies, Foster City, Calif.) were prepared and loaded according to manufacturer's recommendation (Ion Sequencing Kit User Guide v 2.0). The Ion Torrent PGM was run according to Ion Torrent 314 Chip specifications including a 65-cycle sequencing protocol, use of 18 megaOhm purified water, and standard compressed argon gas to drive fluidics through the PGM system. All rpoB, katG, pncA, gyrA and rrs genes and corresponding proteins were deposited into GenBank (accession numbers JX303203-JX303332).

Gyrase PCR for the Detection of TB vs. 6110 PCR Assay.

Figure 7:
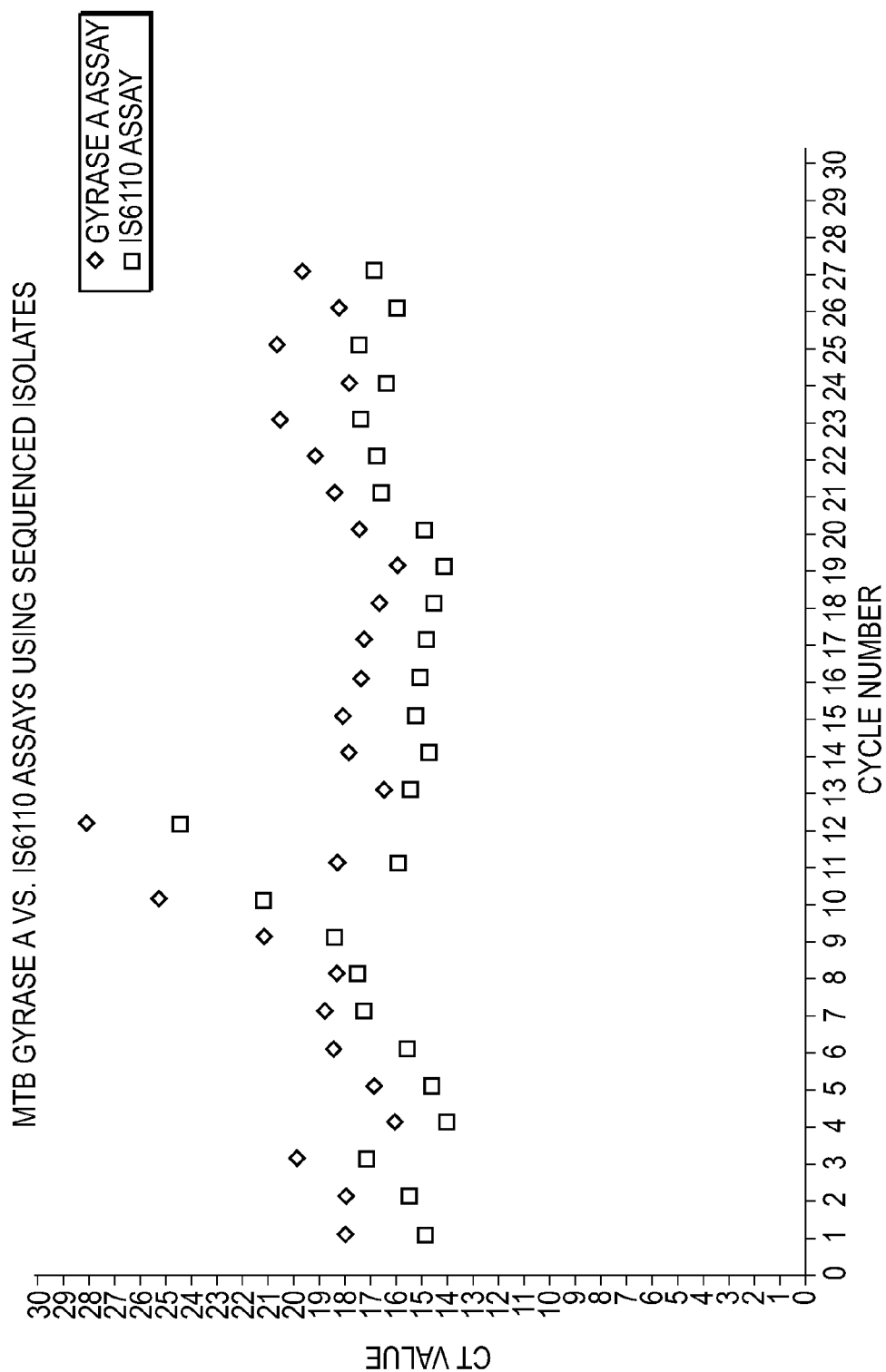
Figure 8:
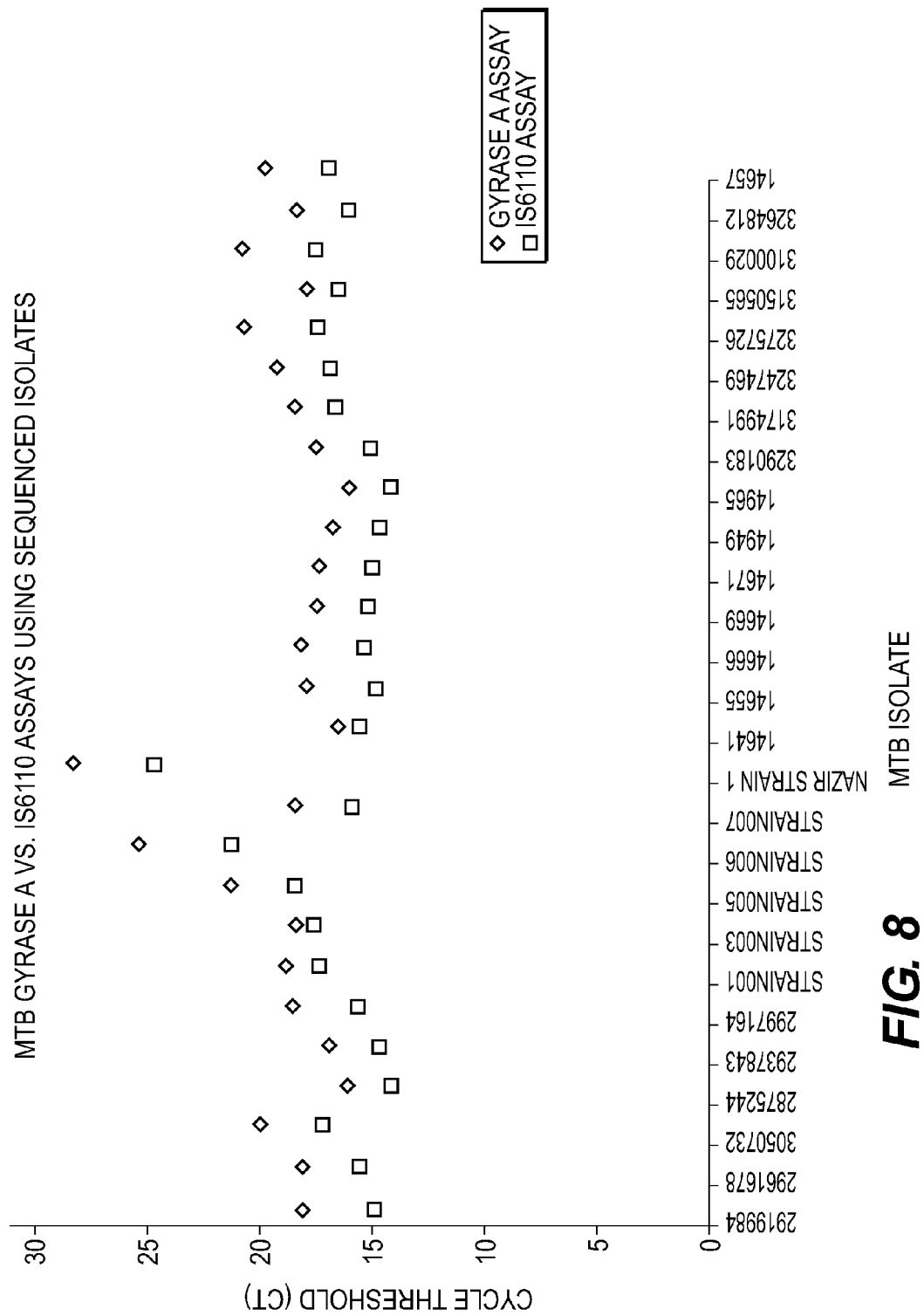

The gyrase target for OCR and whole Gyrase gene sequencing on the Ion Torrent PGM can also be used to identify TB mutations that lead to resistance. This second PCR target allows for the accurate analysis of TB strains that may not include the entire IS6110 insertion element. While the IS6110 assay has multiple gene copies in most strains, some have only one. As shown in FIGS. 6, 7 and 8, this Gyrase assay has a generally higher cycle threshold in comparison to the IS6110 assay due to multiple IS6110 gene copies in those isolates and thus more sensitivity. Thus any possible TB mutation can be followed-even away from the detection site by this method of full gene sequencing.

Phenotypic and Genotypic Results.

Amino Acid characterization of 26 M. tuberculosis isolates by Ion Torrent sequencing of rpoB, katG, pncA, gyrA, and rrs (16s) genes are summarized in Tables 1-5, respectively, and compared to BACTEC™ MGIT™ 960 (phenotypic), and/or HAN GenoType® MTBDRplus (genotypic) LPA. Of the 26 MTB clinical isolates, 14 (54%) were MDR, 7 (27%) were XDR, and 5 (19%) were sensitive to drugs by BACTEC™ MGIT™ 960 phenotypic analysis. The Ion Torrent PGM sequencing method showed 100% (26/26) concordance to both phenotypic resistance obtained by MGIT™ 960 culture (Tables 1-5) and genotypic rpoB and katG data obtained by Hain LPA (Table 1, 2).

rpoB Gene Mutations.

A total of 10 rpoB amino acid substitutions were identified in the 26 clinical isolates compared to the H37Rv wild type strain. The common S531L mutation was the most prevalent, but mutations in codons 516 and 526, also known to confer resistance to rifampin were observed (Table 1). Additionally, mutations were observed within the rpoB open reading frame but outside of the 81-basepair rifampin resistance-determining region (RRDR; Table 1). The V194I mutation observed outside of the RRDR in one strain is a unique substitution that is likely not associated with rifampin resistance. Five amino acid substitutions were noted in at least one strain beyond residue position 900 of the rpoB protein. There were seven strains with an rpoB mutation (6 at position 516 and 1 at position 526) where a wild type band was absent without a corresponding mutation band according to LPA. In six of these seven isolates, Ion Torrent sequencing revealed an uncommon amino acid substitution (i.e. glycine) within a known mutation site at position 516 where a valine (V) substitution (D516V) is typically known to occur (Table 2). Similarly, in one isolate Ion Torrent sequencing revealed an arginine (R) within a known mutation site at position 526 where tyrosine (Y) or aspartic acid (D) substitutions (H526Y/D) typically occur.

katG Gene Mutations.

Four amino acid substitutions were observed in the katG gene with S315T which is known to confer isoniazid resistance present in all resistant strains (Table 2). Clinical strains harboring R463L, W191R, and N138H mutations were detected by DST (Table 2) and have been previously characterized. A substitution at position 463 (R463L) in katG has been previously shown to have no effect on antibiotic resistance and can be used to categorize *M. tuberculosis* isolates into genetic Groups 1 (Arg463) or 2/3 (Leu463). Of 26 clinical isolates assessed, 7 (27%) were members of genetic Group 1 as evident by this R463L substitution.

pncA Gene Mutations.

Seven nucleotide mutations were noted in at least one strain among 561 bps comprising the full-length coding region for the pncA gene (Table 3). Nine of 26 strains (34.6%) contained an amino acid mutation conferring pyrazinamide resistance (Table 3). In one strain, a silent (synonymous) nucleotide mutation was characterized at nucleotide position 195 (C195T). Five strains contained previously characterized amino acid substitutions (C14R, A102V, V 139G, R154G, and L172P) known to confer resistance to pyrazinamide. A novel mutation, not previously reported elsewhere, encoding a termination slop codon was found in one isolate at residue 122 (Q122Stop) in the pncA protein (Table 3).

gyrA Gene Mutations.

Nine unique mutations were observed in the 2,517 bp full-length gyrA gene encoding subunit A of the DNA gyrase enzyme. Resistance to fluoroquinolones (FQ) was only noted in strains harboring mutations in the quinolone resistance determining region (QRDR) defined by substitutions in gyrA at codons 88, 90, and 94. A number of additional mutations were also observed in regions outside of the QRDR including two 'mixed strain' mutations at position 549 and 613 in the gyrA protein (Table 4). Mutation at position 9.5 (S95T) is known to have no effect on FQ resistance but can be used to categorize strains in genetic Groups 2 or 3. Of the 19 total clinical isolates belonging to genetic Groups 2/3, 18 (96%) were Group 2, and 1 (4%) was Group 3 according to assessment of gyrA position 95 (T=genetic Group 2, and S=genetic Group 3).

rrs (16s) Gene Mutations.

Four nucleotide mutations were noted among the 1,540 bps comprising the full length 16s rrs gene. Seven of 26 (27%) clinical isolates were shown to be resistant to aminoglycosides by DST, and all strains harbored an A1401G mutation known to confer resistance (Table 5). Two other amino acid mutations (C492T and A514C) were observed, but have been previously shown to not inhibit aminoglycoside efficacy. A previously uncharacterized G878A nucleotide mutation was observed, but the isolate was shown to be sensitive according to DST (Table 5).

Megabase Sequencing.

Figure 9:
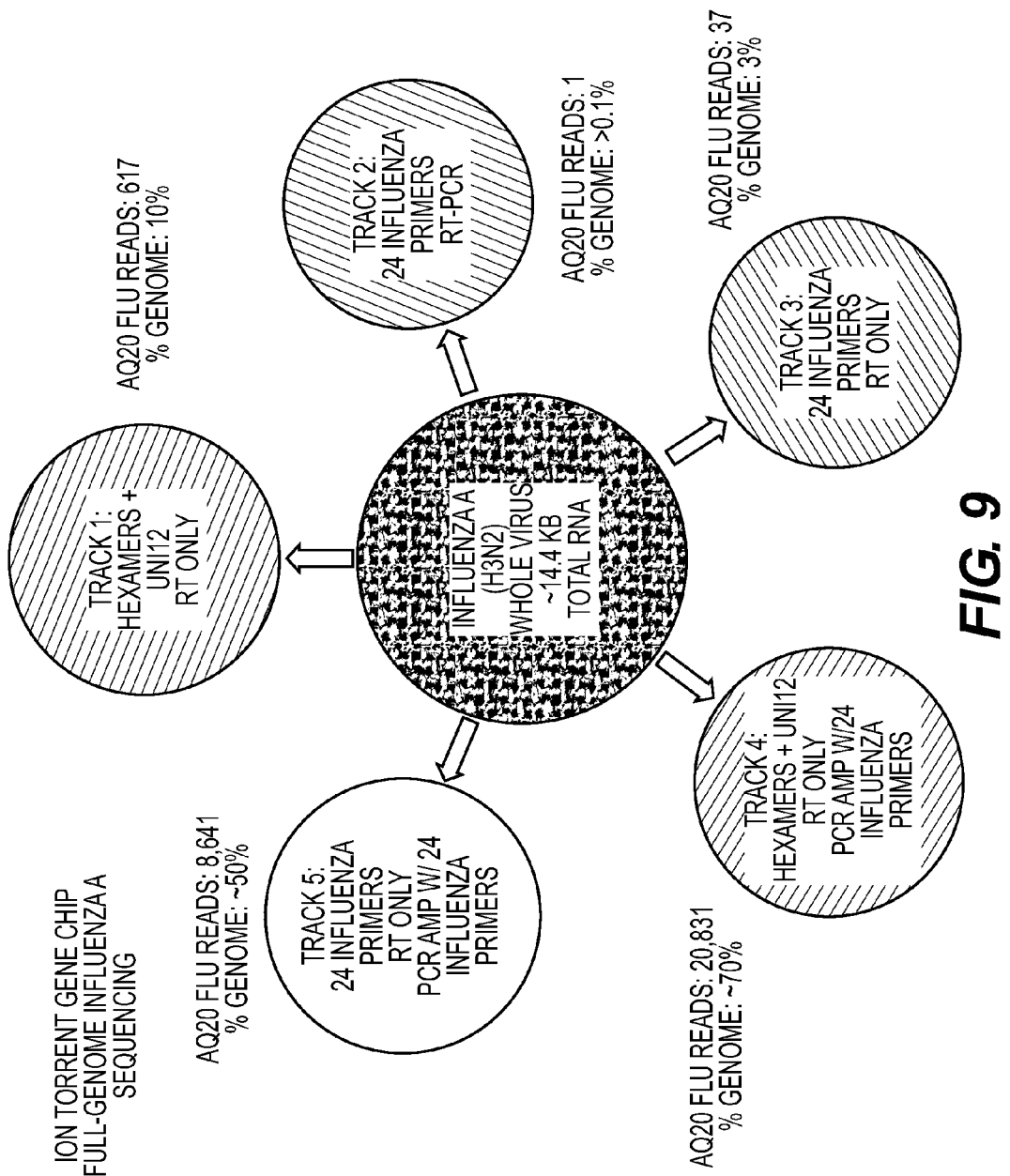

Ion torrent gene chip sequencing was performed on the complete genome of Influenza virus A under five distinct conditions, identified in FIG. 9 as Tracks. Whole viral nucleic acid of Influenza A, strain H3N2 (about 14.4 kb total RNA) was prepared as discussed above and either reverse transcribed only, or reverse transcribed and PCR amplified as indicated in FIG. 9. Influenza virus genome was mass amplified by reverse transcription (RT) and certain amplified cDNA populations subjected to PCR. Each result was then analyzed using the Ion Torrent sequencing protocol. RT and/or RT-PCR analysis was performed with uniform hexamers. Uni 12, and/or 24 different influenza-specific primers (different in both length and sequence). Uniform hexamers comprise a collection of primers, each six nucleotides in length whereby the collections contain all of sequence iterations of the six nucleotides. UM 12 is primer that contains a sequence that is complimentary to 12 nucleotides at the 3' terminus of each of the segments of the influenza H3N2 viral genome (5'-ACGCGTGATCAGCAAAAGCAGG; SEQ ID NO 13). As shown in FIG. 9, Track 4 amplification and sequencing with hexamer primers and Uni 12 followed by PCR amplification with the 24 influenza-specific primers and loll Torrent protocol sequencing identified about 70% of the influenza genome.

Additional experiments were performed to achieve one-step sequencing of the complete Influenza genome. A series of influenza-specific primers were developed that would allow for uniform conditions to be performed for a PCR reaction. The primers that were developed are listed in FIG. 10. These primers are all specific for the influenza virus genome with primer pairs spaced along the genome about every 800 to 1,000 bases in length (see FIG. 10, amplicon length and start and stop positions for primer placement and sequence). All primers were of similar length, about 18-23 nucleotides and contain a similar GC content, about 22.7% to 38.9%, with nearly about 33%±6% and most about 33%±3%. PCR analysis was performed using different collections of these primers and the amplified products identified using the Ion Torrent sequencing protocol.

Sequencing of pncA Gene.

Figures 11, 11B:
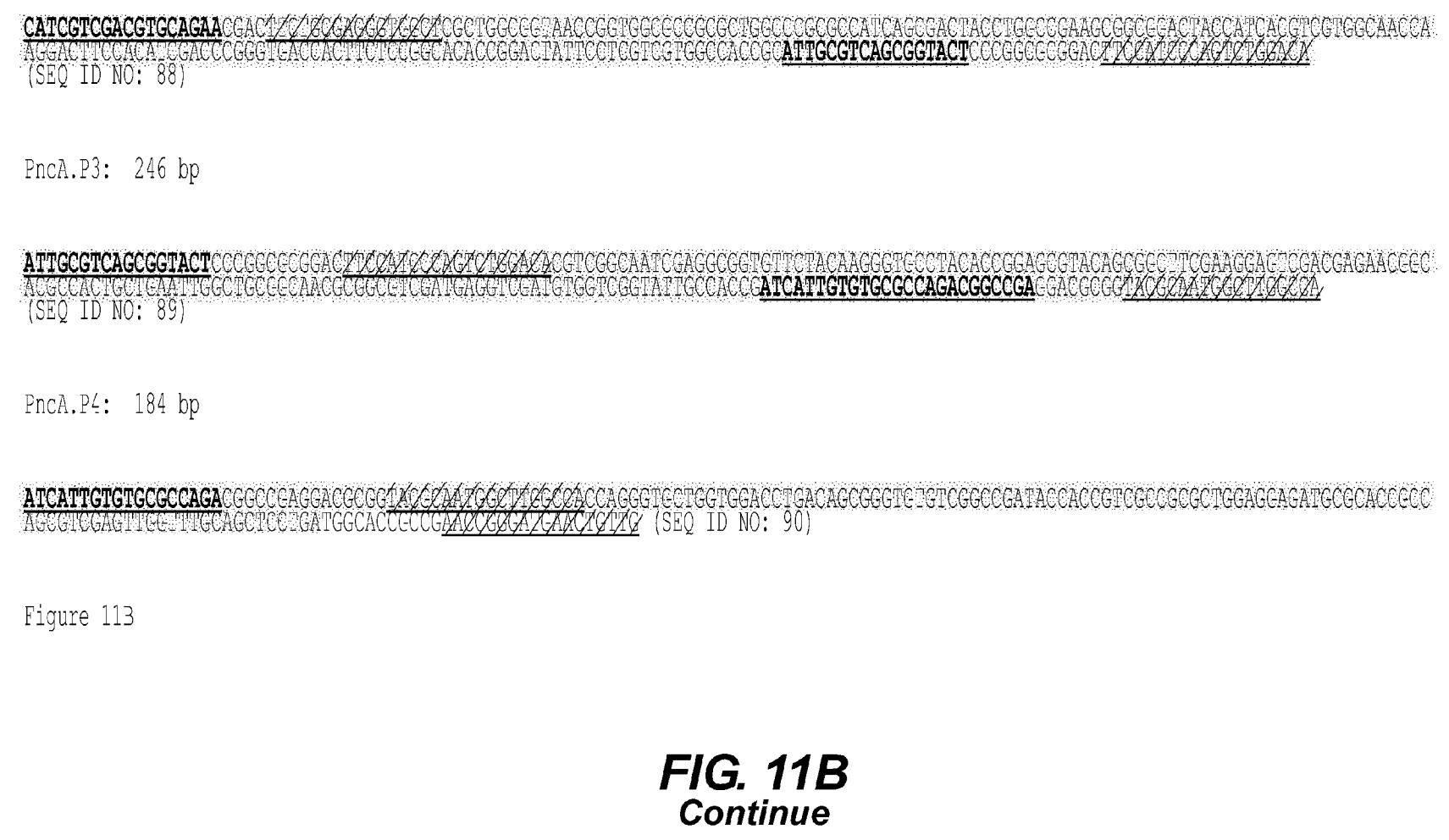

The gene sequence of pncA was determined using a series of primers spaced or "tiled" along the pncA gene in accordance with the invention. The coding sequence of the pncA gene is depicted in FIG. 11A and the primers utilized are depicted in FIG. 11B in bold and underlined. Using these primers in conjunction with Ion Torrent methodology, the entire coding regions of pncA was determined (see P1-P4 of FIG. 11B). Expanding the primers utilized to all genes or of specific regions allows for one-step sequencing of the entire genome.

Other embodiments and uses of the invention will be apparent to those skilled in the art from consideration of the specification and practice of the invention disclosed herein. All references cited herein, including all publications, U.S. and foreign patents and patent applications, are specifically and entirely incorporated by reference. The term comprising, where ever used, is intended to include the terms consisting and consisting essentially of. Furthermore, the terms comprising, including, and containing are not intended to be limiting. It is intended that the specification and examples be considered exemplary only with the true scope and spirit of the invention indicated by the following claims.

The invention claimed is:

1. A method for determining a complete sequence of a target gene or genome of a microorganism, wherein the target gene or genome is greater than 1 Mb in length, comprising:
   producing a series of amplicons by performing a single polymerase chain reaction (PCR) of the target in an aqueous mixture containing a heat-stable polymerase; a mix of deoxynucleotide triphosphates; a chelating agent; a salt; a buffer; a stabilizing agent; and a plurality of primer pairs wherein each primer of the plurality of primer pairs has a similar annealing temperature and wherein each primer pair is designed to PCR amplify an amplicon representing a portion of the sequence of the nucleic acid target, and the series of amplicons that are PCR amplified represent overlapping portions of the complete sequence of the target;
   sequencing each of the series of amplicons by semi-conductor sequencing, and
   correlating the sequences of the amplicons and constructing the complete sequence of the target.

2. The method of claim 1, wherein each of the primers of the multiple primer pairs comprise primers that are from 15 to 25 nucleic acids in length and has a GC content of about 25%-50%.

3. The method of claim 1, wherein each primer pair is designed to PCR amplify an amplicon, and the collection of amplicons that are PCR amplified encompass overlapping segment of the complete sequence of the target.

4. The method of claim 1, wherein the plurality of primer pairs hybridize to the target at intervals of about 500 to 2,000 nucleotides.

5. The method of claim 1, wherein the microorganism is a virus, a bacterium, a fungus, a parasite or a cell.

6. The method of claim 5, wherein the virus is an influenza virus.

7. The method of claim 5, wherein the bacterium is *Mycobacterium tuberculosis*.

8. A method for determining the sequence of a nucleic acid target in one step, wherein the nucleic acid target is greater than 1 Mb in length, comprising:
   performing a polymerase chain reaction on the nucleic acid target to produce a series of amplicons, wherein the reaction comprises: a heat-stable polymerase; a mix of deoxynucleotide triphosphates; a chelating agent; a salt; a buffer; a stabilizing agent; and a plurality of primer pairs wherein each primer of the plurality of primer pairs has an annealing temperature within 5° C. and wherein each primer pair is designed to PCR amplify an amplicon representing a portion of the sequence of the nucleic acid target, and the series of amplicons that are PCR amplified represent overlapping portions of the complete sequence of the target;
   sequencing each of the series of amplicons by semi-conductor sequencing, and
   correlating the sequences of the amplicons and constructing the sequence of the nucleic acid target.

9. The method of claim 8, wherein the nucleic acid target is greater than 5 Mbs in length.

10. The method of claim 8, wherein each of the primers of the multiple primer pairs is from 16 to 24 nucleotides in length, has a GC content of about 28-35%, and an annealing temperature of within 3° C. of each other primer of the multiple primer pairs.

11. The method of claim 8, wherein the plurality of primer pairs hybridizes to the target at a spacing of about 800 to 1,500 nucleotides in length.

12. A method for determining the sequence of a nucleic acid target in one step, wherein the nucleic acid target is greater than 1 Mb in length, comprising:
   performing a polymerase chain reaction on the nucleic acid target to produce a series of amplicons, wherein the reaction comprises: a heat-stable polymerase; a mix of deoxynucleotide triphosphates; a chelating agent; a salt; a buffer; a stabilizing agent; and a plurality of primer pairs wherein each primer of the plurality of primer pairs has an annealing temperature within 5° C., is from 15 to 35 nucleotides in length, has a GC content of about 25-50% and hybridize to the target at intervals of about 500 to 2,000 nucleotides and further wherein each primer pair is designed to PCR amplify an amplicon representing a portion of the sequence of the nucleic acid target, and the series of amplicons that are PCR amplified represent overlapping portions of the complete sequence of the target;
   sequencing each of the series of amplicons by semi-conductor sequencing, and
   correlating the sequences of the amplicons and constructing the sequence of the nucleic acid target.

13. The method of claim 12, wherein each of the primers of the multiple primer pairs is from 16 to 24 nucleotides in length, has a GC content of about 28-35%, and an annealing temperature of within 3° C. of each other primer of the multiple primer pairs.

14. The method of claim 12, wherein the nucleic acid target comprises a sequence of a virus, bacteria, fungus or parasite.

15. The method of claim 14, wherein the virus is an influenza virus.

16. The method of claim 14, wherein the bacterium is a *Mycobacterium tuberculosis*.

17. The method of claim 12, wherein the nucleic acid target comprises a complete sequence of a target gene or genome of a microorganism.

18. The method of claim 17, wherein the nucleic acid target sequence constructed correlates with resistance of the microorganism to an antimicrobial compound.

19. The method of claim 18, wherein the antimicrobial compound is an antibiotic.

* * * * *